United States Patent
Kveen et al.

(10) Patent No.: US 9,662,487 B2
(45) Date of Patent: *May 30, 2017

(54) DELIVERY OF CARDIAC STIMULATION DEVICES

(71) Applicant: BOSTON SCIENTIFIC SCIMED, INC., Maple Grove, MN (US)

(72) Inventors: Graig L. Kveen, Maple Grove, MN (US); Douglas R. Saholt, Mound, MN (US); Roger N. Hastings, Maple Grove, MN (US); Richard C. Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 5 days.

This patent is subject to a terminal disclaimer.

(21) Appl. No.: 15/058,941

(22) Filed: Mar. 2, 2016

(65) Prior Publication Data

US 2016/0175583 A1 Jun. 23, 2016

Related U.S. Application Data

(60) Continuation of application No. 13/476,599, filed on May 21, 2012, now Pat. No. 9,308,374, which is a
(Continued)

(51) Int. Cl.
*A61N 1/05* (2006.01)
*A61N 1/362* (2006.01)
(Continued)

(52) U.S. Cl.
CPC ........... *A61N 1/0573* (2013.01); *A61N 1/362* (2013.01); *A61N 1/3756* (2013.01);
(Continued)

(58) Field of Classification Search
CPC ...... A61N 1/056; A61N 1/057; A61N 1/0587; A61N 1/059; A61N 1/372; A61N 1/37205
See application file for complete search history.

(56) References Cited

U.S. PATENT DOCUMENTS 3,057,356 A 10/1962 Greatbatch
3,357,434 A 12/1967 Abell
(Continued)

FOREIGN PATENT DOCUMENTS

EP 0758542 A1 2/1997
EP 0904009 A1 3/1999
(Continued)

OTHER PUBLICATIONS

"U.S. Appl. No. 11/316,120, Response filed Jul. 17, 2009 to Non Final Office Action mailed Apr. 17, 2009", 13 pgs.
(Continued)

*Primary Examiner* — Joseph Dietrich
(74) *Attorney, Agent, or Firm* — Seager, Tufte & Wickhem LLP

(57) ABSTRACT

Some embodiments of an electrical stimulation system employ wireless electrode assemblies to provide pacing therapy, defibrillation therapy, or other stimulation therapy. In certain embodiments, the wireless electrode assemblies may include a guide wire channel so that each electrode assembly can be advanced over a guide wire instrument through the endocardium. For example, a distal tip portion of a guide wire instrument can penetrate through the endocardium and into the myocardial wall of a heart chamber, and the electrode assembly may then be advanced over the guide wire and into the heart chamber wall. In such circumstances, the guide wire instrument (and other portions of the
(Continued)

delivery system) can be retracted from the heart chamber wall, thereby leaving the electrode assembly embedded in the heart tissue.

18 Claims, 10 Drawing Sheets

Related U.S. Application Data continuation of application No. 12/910,106, filed on Oct. 22, 2010, now Pat. No. 8,185,213, which is a division of application No. 11/490,916, filed on Jul. 21, 2006, now Pat. No. 7,840,281.

(51) Int. Cl.
A61N 1/372 (2006.01)
A61N 1/375 (2006.01)
A61M 25/00 (2006.01)

(52) U.S. Cl.
CPC ..... *A61N 1/37205* (2013.01); *A61M 25/0082* (2013.01); *A61M 2025/0095* (2013.01); *A61N 1/37288* (2013.01)

(56) References Cited

U.S. PATENT DOCUMENTS

| | | |
|---|---|---|
| 3,596,662 A | 8/1971 | Bolduc |
| 3,667,477 A | 6/1972 | Susset et al. |
| 3,713,449 A | 1/1973 | Mulier |
| 3,727,616 A | 4/1973 | Lenzkes |
| 3,835,864 A | 9/1974 | Rasor et al. |
| 3,902,501 A | 9/1975 | Citron et al. |
| 3,942,535 A | 3/1976 | Schulman |
| 3,943,936 A | 3/1976 | Rasor et al. |
| 4,010,756 A | 3/1977 | DuMont et al. |
| 4,157,720 A | 6/1979 | Greatbatch |
| 4,162,679 A | 7/1979 | Reenstierna |
| 4,198,991 A | 4/1980 | Harris |
| 4,256,115 A | 3/1981 | Bilitch |
| 4,441,210 A | 4/1984 | Hochmair et al. |
| 4,525,774 A | 6/1985 | Kino et al. |
| 4,543,955 A | 10/1985 | Schroeppel |
| 4,641,664 A | 2/1987 | Botvidsson |
| 4,644,957 A | 2/1987 | Ricciardelli et al. |
| 4,681,111 A | 7/1987 | Silvian |
| 4,721,118 A | 1/1988 | Harris |
| 4,830,006 A | 5/1989 | Haluska et al. |
| 4,858,623 A | 8/1989 | Bradshaw et al. |
| 4,860,750 A | 8/1989 | Frey et al. |
| 4,913,164 A | 4/1990 | Greene et al. |
| 4,953,564 A | 9/1990 | Berthelsen |
| 4,987,897 A | 1/1991 | Funke |
| 5,012,806 A | 5/1991 | De Bellis |
| 5,078,736 A | 1/1992 | Behl |
| 5,113,869 A | 5/1992 | Nappholz et al. |
| 5,139,033 A | 8/1992 | Everett et al. |
| 5,143,090 A | 9/1992 | Dutcher et al. |
| 5,170,802 A | 12/1992 | Mehra |
| 5,178,149 A | 1/1993 | Imburgia et al. |
| 5,193,539 A | 3/1993 | Schulman et al. |
| 5,193,540 A | 3/1993 | Schulman et al. |
| 5,234,437 A | 8/1993 | Sepetka |
| 5,243,977 A | 9/1993 | Trabucco et al. |
| 5,246,014 A | 9/1993 | Williams et al. |
| 5,250,071 A | 10/1993 | Palermo |
| 5,255,693 A | 10/1993 | Dutcher et al. |
| 5,261,916 A | 11/1993 | Engelson |
| 5,300,107 A | 4/1994 | Stokes et al. |
| 5,304,195 A | 4/1994 | Twyford, Jr. et al. |
| 5,312,415 A | 5/1994 | Palermo |
| 5,312,439 A | 5/1994 | Loeb |
| 5,314,458 A | 5/1994 | Najafi et al. |
| 5,324,316 A | 6/1994 | Schulman et al. |
| 5,324,325 A | 6/1994 | Moaddeb |
| 5,335,664 A | 8/1994 | Nagashima |
| 5,336,252 A | 8/1994 | Cohen |
| 5,342,408 A | 8/1994 | deCoriolis et al. |
| 5,350,397 A | 9/1994 | Palermo et al. |
| 5,383,915 A | 1/1995 | Adams |
| 5,383,924 A | 1/1995 | Brehier |
| 5,405,367 A | 4/1995 | Schulman et al. |
| 5,411,535 A | 5/1995 | Fujii et al. |
| 5,411,537 A | 5/1995 | Munshi et al. |
| 5,447,533 A | 9/1995 | Vachon et al. |
| 5,487,760 A | 1/1996 | Villafana |
| 5,531,780 A | 7/1996 | Vachon |
| 5,571,148 A | 11/1996 | Loeb et al. |
| 5,591,217 A | 1/1997 | Barreras |
| 5,622,168 A | 4/1997 | Keusch et al. |
| 5,624,316 A | 4/1997 | Roskowski et al. |
| 5,628,778 A | 5/1997 | Kruse et al. |
| 5,674,259 A | 10/1997 | Gray |
| 5,735,887 A | 4/1998 | Barreras, Sr. et al. |
| 5,755,764 A | 5/1998 | Schroeppel |
| 5,769,877 A | 6/1998 | Barreras, Sr. |
| 5,772,693 A | 6/1998 | Brownlee |
| 5,775,331 A | 7/1998 | Raymond et al. |
| 5,779,715 A | 7/1998 | Tu |
| 5,792,208 A | 8/1998 | Gray |
| 5,800,535 A | 9/1998 | Howard, III |
| 5,807,397 A | 9/1998 | Barreras |
| 5,814,089 A | 9/1998 | Stokes et al. |
| 5,833,715 A | 11/1998 | Vachon et al. |
| 5,851,227 A | 12/1998 | Spehr |
| 5,861,019 A | 1/1999 | Sun et al. |
| 5,871,532 A | 2/1999 | Schroeppel |
| 5,876,429 A | 3/1999 | Schroeppel |
| 5,876,431 A | 3/1999 | Spehr et al. |
| 5,954,757 A | 9/1999 | Gray |
| 5,995,876 A | 11/1999 | Kruse et al. |
| 6,006,139 A | 12/1999 | Kruse et al. |
| 6,035,239 A | 3/2000 | Patag et al. |
| 6,041,258 A | 3/2000 | Cigaina et al. |
| 6,044,300 A | 3/2000 | Gray |
| 6,053,873 A | 4/2000 | Govari et al. |
| 6,115,636 A | 9/2000 | Ryan |
| 6,123,724 A | 9/2000 | Denker |
| 6,132,456 A | 10/2000 | Sommer et al. |
| 6,141,588 A | 10/2000 | Cox et al. |
| 6,141,591 A | 10/2000 | Lenarz et al. |
| 6,144,879 A | 11/2000 | Gray |
| 6,144,880 A | 11/2000 | Ding et al. |
| 6,161,029 A | 12/2000 | Spreigl et al. |
| 6,164,284 A | 12/2000 | Schulman et al. |
| 6,200,303 B1 | 3/2001 | Verrior et al. |
| 6,208,894 B1 | 3/2001 | Schulman et al. |
| 6,223,079 B1 | 4/2001 | Bakels et al. |
| 6,240,316 B1 | 5/2001 | Richmond et al. |
| 6,266,567 B1 | 7/2001 | Ishikawa et al. |
| 6,315,721 B2 | 11/2001 | Schulman et al. |
| 6,317,615 B1 | 11/2001 | KenKnight et al. |
| 6,322,559 B1 | 11/2001 | Daulton et al. |
| 6,336,937 B1 | 1/2002 | Vonesh et al. |
| 6,345,202 B2 | 2/2002 | Richmond et al. |
| 6,351,673 B1 | 2/2002 | Ding et al. |
| 6,360,127 B1 | 3/2002 | Ding et al. |
| 6,363,279 B1 | 3/2002 | Ben-Haim et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,409,674 B1 | 6/2002 | Brockway et al. |
| 6,441,747 B1 | 8/2002 | Khair et al. |
| 6,442,413 B1 | 8/2002 | Silver |
| 6,445,953 B1 | 9/2002 | Bulkes et al. |
| 6,456,256 B1 | 9/2002 | Amundson et al. |
| 6,501,983 B1 | 12/2002 | Natarajan et al. |
| 6,510,345 B1 | 1/2003 | Van Bentem |
| 6,522,926 B1 | 2/2003 | Kieval et al. |
| 6,542,775 B2 | 4/2003 | Ding et al. |
| 6,556,874 B2 | 4/2003 | Audoglio |
| 6,564,807 B1 | 5/2003 | Schulman et al. |

(56) References Cited

U.S. PATENT DOCUMENTS

| | | |
|---|---|---|
| 6,571,127 B1 | 5/2003 | Ben-Haim et al. |
| 6,574,510 B2 | 6/2003 | Von Arx et al. |
| 6,582,441 B1 | 6/2003 | He et al. |
| 6,589,230 B2 | 7/2003 | Gia et al. |
| 6,614,406 B2 | 9/2003 | Amundson et al. |
| 6,647,291 B1 | 11/2003 | Bonner et al. |
| 6,647,292 B1 | 11/2003 | Bardy et al. |
| 6,783,499 B2 | 8/2004 | Schwartz |
| 6,856,836 B2 | 2/2005 | Ding et al. |
| 6,859,665 B2 | 2/2005 | Ding et al. |
| 6,895,265 B2 | 5/2005 | Silver |
| 6,895,280 B2 | 5/2005 | Meadows et al. |
| 6,897,788 B2 | 5/2005 | Khair et al. |
| 6,901,294 B1 | 5/2005 | Whitehurst et al. |
| 6,907,285 B2 | 6/2005 | Denker et al. |
| 6,917,833 B2 | 7/2005 | Denker et al. |
| 6,947,792 B2 | 9/2005 | Ben-Haim et al. |
| 6,970,742 B2 | 11/2005 | Mann et al. |
| 6,978,173 B2 | 12/2005 | Stoll et al. |
| 7,003,350 B2 | 2/2006 | Denker et al. |
| 7,006,864 B2 | 2/2006 | Echt et al. |
| 7,050,849 B2 | 5/2006 | Echt et al. |
| 7,054,691 B1 | 5/2006 | Kuzma et al. |
| 7,062,318 B2 | 6/2006 | Ben-Haim et al. |
| 7,076,305 B2 | 7/2006 | Imran et al. |
| 7,184,830 B2 | 2/2007 | Echt et al. |
| 7,200,437 B1 | 4/2007 | Nabutovsky et al. |
| 7,209,783 B2 | 4/2007 | Fellows et al. |
| 7,231,260 B2 | 6/2007 | Wallace et al. |
| 7,289,853 B1 | 10/2007 | Campbell et al. |
| 7,410,497 B2 | 8/2008 | Hastings et al. |
| 7,522,962 B1 | 4/2009 | Doron et al. |
| 7,532,932 B2 | 5/2009 | Denker et al. |
| 7,532,933 B2 | 5/2009 | Hastings et al. |
| 7,558,631 B2 | 7/2009 | Cowan et al. |
| 7,565,195 B1 | 7/2009 | Kroll et al. |
| 7,606,621 B2 | 10/2009 | Brisken et al. |
| 7,610,092 B2 | 10/2009 | Cowan et al. |
| 7,615,010 B1 | 11/2009 | Najafi et al. |
| 7,634,313 B1 | 12/2009 | Kroll et al. |
| 7,647,109 B2 | 1/2010 | Hastings et al. |
| 7,650,186 B2 | 1/2010 | Hastings et al. |
| 7,702,392 B2 | 4/2010 | Echt et al. |
| 7,765,001 B2 | 7/2010 | Echt et al. |
| 7,809,438 B2 | 10/2010 | Echt et al. |
| 7,840,281 B2 | 11/2010 | Kveen et al. |
| 7,848,815 B2 | 12/2010 | Brisken et al. |
| 7,848,823 B2 | 12/2010 | Drasler et al. |
| 7,877,136 B1 | 1/2011 | Moffitt et al. |
| 7,877,142 B2 | 1/2011 | Moaddeb et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,904,170 B2 | 3/2011 | Harding |
| 7,937,148 B2 | 5/2011 | Jacobson |
| 7,937,161 B2 | 5/2011 | Hastings et al. |
| 7,945,333 B2 | 5/2011 | Jacobson |
| 7,996,087 B2 | 8/2011 | Cowan et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,050,774 B2 | 11/2011 | Kveen et al. |
| 8,165,694 B2 | 4/2012 | Carbanaru et al. |
| 8,185,213 B2 | 5/2012 | Kveen et al. |
| 8,204,595 B2 | 6/2012 | Pianca et al. |
| 8,204,605 B2 | 6/2012 | Hastings et al. |
| 8,260,416 B2 | 9/2012 | Ben-Haim et al. |
| 8,290,600 B2 | 10/2012 | Hastings et al. |
| 8,332,036 B2 | 12/2012 | Hastings et al. |
| 8,340,780 B2 | 12/2012 | Hastings et al. |
| 8,352,025 B2 | 1/2013 | Jacobson |
| 8,478,408 B2 | 7/2013 | Hastings et al. |
| 8,644,934 B2 | 2/2014 | Hastings et al. |
| 2001/0018547 A1 | 8/2001 | Mechlenburg |
| 2002/0026228 A1 | 2/2002 | Schauerte |
| 2002/0052632 A1 | 5/2002 | Ben-Haim et al. |
| 2002/0065543 A1 | 5/2002 | Gomperz et al. |
| 2002/0077556 A1 | 6/2002 | Schwartz |
| 2002/0077685 A1 | 6/2002 | Sundquist et al. |
| 2002/0123774 A1 | 9/2002 | Loeb et al. |
| 2002/0123785 A1 | 9/2002 | Zhang et al. |
| 2002/0128546 A1 | 9/2002 | Silver |
| 2002/0138009 A1 | 9/2002 | Brockway et al. |
| 2002/0138100 A1 | 9/2002 | Stoll et al. |
| 2002/0183791 A1 | 12/2002 | Denker et al. |
| 2002/0188323 A1 | 12/2002 | Penner et al. |
| 2002/0198604 A1 | 12/2002 | Schulman et al. |
| 2003/0036773 A1 | 2/2003 | Whitehurst et al. |
| 2003/0050681 A1 | 3/2003 | Pianca et al. |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0074041 A1 | 4/2003 | Parry et al. |
| 2003/0088278 A1 | 5/2003 | Bardy et al. |
| 2003/0109914 A1 | 6/2003 | Westlund et al. |
| 2003/0114735 A1 | 6/2003 | Silver et al. |
| 2003/0114742 A1 | 6/2003 | Lewkowicz et al. |
| 2003/0158584 A1 | 8/2003 | Cates et al. |
| 2003/0172388 A1 | 9/2003 | Fujise et al. |
| 2003/0181958 A1 | 9/2003 | Dobak, III |
| 2003/0181959 A1 | 9/2003 | Dobak, III |
| 2003/0204206 A1 | 10/2003 | Padua et al. |
| 2003/0216729 A1 | 11/2003 | Marchitto et al. |
| 2003/0236518 A1 | 12/2003 | Marchitto et al. |
| 2004/0019364 A1 | 1/2004 | Kieval et al. |
| 2004/0059280 A1 | 3/2004 | Makower et al. |
| 2004/0059392 A1 | 3/2004 | Parramon et al. |
| 2004/0073267 A1 | 4/2004 | Holzer |
| 2004/0087831 A1 | 5/2004 | Michels et al. |
| 2004/0097805 A1 | 5/2004 | Verard et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0127895 A1 | 7/2004 | Flock et al. |
| 2004/0147969 A1 | 7/2004 | Mann et al. |
| 2004/0147973 A1 | 7/2004 | Hauser |
| 2004/0167580 A1 | 8/2004 | Mann et al. |
| 2004/0171355 A1 | 9/2004 | Yu et al. |
| 2004/0172083 A1 | 9/2004 | Penner |
| 2004/0176672 A1 | 9/2004 | Silver et al. |
| 2004/0176822 A1 | 9/2004 | Thompson et al. |
| 2004/0193092 A1 | 9/2004 | Deal |
| 2004/0193229 A1 | 9/2004 | Starkebaum et al. |
| 2004/0210282 A1 | 10/2004 | Flock et al. |
| 2004/0215092 A1 | 10/2004 | Fischell et al. |
| 2004/0215280 A1 | 10/2004 | Dublin et al. |
| 2004/0230090 A1 | 11/2004 | Hegde et al. |
| 2004/0230255 A1 | 11/2004 | Dobak, III |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0051243 A1 | 3/2005 | Forbes Jones et al. |
| 2005/0057905 A1 | 3/2005 | He et al. |
| 2005/0065575 A1 | 3/2005 | Dobak |
| 2005/0080346 A1 | 4/2005 | Gianchandani et al. |
| 2005/0080459 A1 | 4/2005 | Jacobson et al. |
| 2005/0095197 A1 | 5/2005 | Tuszynski et al. |
| 2005/0096702 A1 | 5/2005 | Denker et al. |
| 2005/0131511 A1 | 6/2005 | Westlund |
| 2005/0136385 A1 | 6/2005 | Mann et al. |
| 2005/0149138 A1 | 7/2005 | Min et al. |
| 2005/0165456 A1 | 7/2005 | Mann et al. |
| 2005/0182456 A1 | 8/2005 | Ziobro et al. |
| 2005/0182465 A1 | 8/2005 | Ness |
| 2005/0192637 A1 | 9/2005 | Girouard et al. |
| 2005/0215764 A1 | 9/2005 | Tuszynski et al. |
| 2005/0245846 A1 | 11/2005 | Casey |
| 2005/0249667 A1 | 11/2005 | Tuszynski et al. |
| 2005/0251238 A1 | 11/2005 | Wallace et al. |

(56) References Cited

U.S. PATENT DOCUMENTS

| | | |
|---|---|---|
| 2005/0251240 A1 | 11/2005 | Doan |
| 2005/0256549 A1 | 11/2005 | Holzer |
| 2005/0261741 A1 | 11/2005 | Libbus et al. |
| 2005/0273014 A1 | 12/2005 | Gianchandani et al. |
| 2005/0288596 A1 | 12/2005 | Eigler et al. |
| 2005/0288717 A1 | 12/2005 | Sunagawa |
| 2005/0288727 A1 | 12/2005 | Penner |
| 2006/0015097 A1 | 1/2006 | Mulier et al. |
| 2006/0020316 A1 | 1/2006 | Martinez et al. |
| 2006/0064135 A1 | 3/2006 | Brockway |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095089 A1 | 5/2006 | Soykan et al. |
| 2006/0136001 A1 | 6/2006 | Ortega et al. |
| 2006/0136004 A1 | 6/2006 | Cowan et al. |
| 2006/0173504 A1 | 8/2006 | Zhu et al. |
| 2006/0173505 A1 | 8/2006 | Salo et al. |
| 2006/0178719 A1 | 8/2006 | Ideker et al. |
| 2006/0206170 A1 | 9/2006 | Denker et al. |
| 2006/0241705 A1 | 10/2006 | Neumann et al. |
| 2007/0075905 A1 | 4/2007 | Denker et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088418 A1 | 4/2007 | Jacobson |
| 2007/0106357 A1 | 5/2007 | Denker et al. |
| 2007/0135882 A1 | 6/2007 | Drasler et al. |
| 2007/0135883 A1 | 6/2007 | Drasler et al. |
| 2007/0150009 A1 | 6/2007 | Kveen et al. |
| 2007/0150037 A1 | 6/2007 | Hastings et al. |
| 2007/0150038 A1 | 6/2007 | Hastings et al. |
| 2007/0162079 A1 | 7/2007 | Shemer et al. |
| 2007/0203556 A1 | 8/2007 | Rutten et al. |
| 2007/0219590 A1 | 9/2007 | Hastings et al. |
| 2007/0239248 A1 | 10/2007 | Hastings et al. |
| 2007/0276444 A1 | 11/2007 | Gelbart et al. |
| 2007/0293904 A1 | 12/2007 | Gelbart et al. |
| 2008/0021505 A1 | 1/2008 | Hastings et al. |
| 2008/0021532 A1 | 1/2008 | Kveen et al. |
| 2008/0039904 A1 | 2/2008 | Bulkes et al. |
| 2008/0046040 A1 | 2/2008 | Denker et al. |
| 2008/0077184 A1 | 3/2008 | Denker et al. |
| 2008/0077188 A1 | 3/2008 | Denker et al. |
| 2008/0109054 A1 | 5/2008 | Hastings et al. |
| 2008/0119911 A1 | 5/2008 | Rosero |
| 2008/0140142 A1 | 6/2008 | Darvish et al. |
| 2008/0262588 A1 | 10/2008 | Zarembo et al. |
| 2008/0288039 A1 | 11/2008 | Reddy |
| 2008/0306359 A1 | 12/2008 | Zdeblick et al. |
| 2008/0319502 A1 | 12/2008 | Sunagawa et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0204170 A1 | 8/2009 | Hastings et al. |
| 2009/0234407 A1 | 9/2009 | Hastings et al. |
| 2009/0275998 A1 | 11/2009 | Burnes et al. |
| 2010/0094367 A1 | 4/2010 | Sen |
| 2010/0100144 A1 | 4/2010 | Shuros et al. |
| 2010/0198288 A1 | 8/2010 | Ostroff |
| 2010/0228308 A1 | 9/2010 | Cowan et al. |
| 2010/0286744 A1 | 11/2010 | Echt et al. |
| 2010/0314775 A1 | 12/2010 | Schwarzbauer |
| 2011/0034939 A1 | 2/2011 | Kveen et al. |
| 2011/0071586 A1 | 3/2011 | Jacobson |
| 2011/0077708 A1 | 3/2011 | Ostroff |
| 2011/0190835 A1 | 8/2011 | Brockway et al. |
| 2011/0208260 A1 | 8/2011 | Jacobson |
| 2011/0213233 A1 | 9/2011 | Stevenson et al. |
| 2011/0218587 A1 | 9/2011 | Jacobson |
| 2011/0237967 A1 | 9/2011 | Moore et al. |
| 2011/0251660 A1 | 10/2011 | Griswold |
| 2011/0251662 A1 | 10/2011 | Griswold et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2012/0078322 A1 | 3/2012 | Dal Molin et al. |
| 2012/0089198 A1 | 4/2012 | Ostroff |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0158111 A1 | 6/2012 | Khairkhahan et al. |
| 2012/0172690 A1 | 7/2012 | Anderson et al. |
| 2013/0268042 A1 | 10/2013 | Hastings et al. |

FOREIGN PATENT DOCUMENTS

| | | |
|---|---|---|
| EP | 1166820 A2 | 1/2002 |
| EP | 1166832 A1 | 1/2002 |
| EP | 1264572 A1 | 12/2002 |
| EP | 0904009 B1 | 9/2003 |
| EP | 1809372 A2 | 7/2007 |
| EP | 1812104 A1 | 8/2007 |
| EP | 1835962 A1 | 9/2007 |
| FR | 2559391 A1 | 8/1985 |
| JP | 61203730 A | 9/1986 |
| JP | 62254770 A | 11/1987 |
| JP | 02307481 A | 12/1990 |
| JP | 05076501 A | 3/1993 |
| JP | 05245215 A | 9/1993 |
| JP | 6510459 A | 11/1994 |
| JP | 7016299 A | 1/1995 |
| JP | 9508054 A | 8/1997 |
| JP | 2000502931 A | 3/2000 |
| JP | 2001511406 A | 8/2001 |
| JP | 2002510222 A | 4/2002 |
| JP | 2002514478 A | 5/2002 |
| JP | 2004173790 A | 6/2004 |
| JP | 2005245215 A | 9/2005 |
| JP | 2010509901 A | 3/2010 |
| NZ | 526115 A | 10/2006 |
| NZ | 539770 A | 10/2007 |
| NZ | 539771 A | 10/2007 |
| WO | 9116864 A1 | 11/1991 |
| WO | 9308871 A1 | 5/1993 |
| WO | 9510226 A1 | 4/1995 |
| WO | 9620754 A1 | 7/1996 |
| WO | 9639932 A1 | 12/1996 |
| WO | 9725098 A1 | 7/1997 |
| WO | 9745157 A1 | 12/1997 |
| WO | 9826840 A1 | 6/1998 |
| WO | 9829030 A1 | 7/1998 |
| WO | 9857592 A1 | 12/1998 |
| WO | 9903533 A1 | 1/1999 |
| WO | 9906102 A1 | 2/1999 |
| WO | 9958191 A1 | 11/1999 |
| WO | 9964104 A1 | 12/1999 |
| WO | 0030534 A1 | 6/2000 |
| WO | 0100114 A1 | 1/2001 |
| WO | 0187137 A2 | 11/2001 |
| WO | 03041793 A2 | 5/2003 |
| WO | 03053491 A2 | 7/2003 |
| WO | 03076010 A1 | 9/2003 |
| WO | 03082403 A2 | 10/2003 |
| WO | 03096918 A1 | 11/2003 |
| WO | 03099102 A2 | 12/2003 |
| WO | 2004002572 A1 | 1/2004 |
| WO | 2004012811 A1 | 2/2004 |
| WO | 2004032788 A2 | 4/2004 |
| WO | 2004078025 A2 | 9/2004 |
| WO | 2005058143 A2 | 6/2005 |
| WO | 2005096954 A2 | 10/2005 |
| WO | 2005101660 A1 | 10/2005 |
| WO | 2005107852 A1 | 11/2005 |
| WO | 2005107863 A2 | 11/2005 |
| WO | 2005117737 A2 | 12/2005 |
| WO | 2006045073 A1 | 4/2006 |
| WO | 2006045074 A2 | 4/2006 |

(56) References Cited

FOREIGN PATENT DOCUMENTS

| WO | 2006045075 A1 | 4/2006 |
|---|---|---|
| WO | 2006096685 A1 | 9/2006 |
| WO | 2007067231 A1 | 6/2007 |
| WO | 2007067253 A1 | 6/2007 |
| WO | 2007078770 A2 | 7/2007 |
| WO | 2007115044 A2 | 10/2007 |
| WO | 2008011626 A1 | 1/2008 |
| WO | 2007115044 A3 | 2/2008 |
| WO | 2008034005 A2 | 3/2008 |
| WO | 2008111998 A1 | 9/2008 |
| WO | 2009099550 A1 | 8/2009 |
| WO | 2009099597 A1 | 8/2009 |
| WO | 2012082755 A1 | 6/2012 |

OTHER PUBLICATIONS

"U.S. Appl. No. 11/316,120, Response filed Aug. 27, 2010 to Non Final Office Action mailed May 27, 2010", 13 pgs.
"U.S. Appl. No. 11/316,120, Response filed Dec. 22, 2008 to Final Office Action mailed Aug. 20, 2008", 13 pgs.
"U.S. Appl. No. 11/316,120, Supplemental Notice of Allowance mailed Sep. 1, 2011", 4 pgs.
"U.S. Appl. No. 11/394,601, Decision on Pre-Appeal Brief Request mailed Oct. 6, 2010", 2 pgs.
"U.S. Appl. No. 11/394,601, Final Office Action mailed Mar. 22, 2010", 7 pgs.
"U.S. Appl. No. 11/394,601, Non-Final Office Action mailed Sep. 2, 2009", 7 pgs.
"U.S. Appl. No. 11/394,601, Notice of Allowance mailed Dec. 28, 2010", 8 pgs.
"U.S. Appl. No. 11/394,601, Pre-Appeal Brief Request mailed Jul. 21, 2010", 5 pgs.
"U.S. Appl. No. 11/394,601, Response filed Dec. 2, 2009 to Non Final Office Action mailed Sep. 2, 2009", 11 pgs.
"U.S. Appl. No. 11/394,601, Restriction Requirement mailed Apr. 2, 2009", 10 pgs.
"U.S. Appl. No. 11/490,576, Decision on Pre-Appeal Brief Request mailed Aug. 30, 2011" 2 pgs.
"U.S. Appl. No. 11/490,576, Final Office Action mailed Jan. 19, 2011", 12 pgs.
"U.S. Appl. No. 11/490,576, Non Final Office Action mailed Jul. 9, 2008", 16 pgs.
"U.S. Appl. No. 11/490,576, Non Final Office Action mailed Nov. 9, 2011", 9 pgs.
"U.S. Appl. No. 11/490,576, Non Final Office Action mailed Feb. 17, 2009", 8 pgs.
"U.S. Appl. No. 11/490,576, Non Final Office Action mailed Jul. 12, 2010", 8 pgs.
"U.S. Appl. No. 11/490,576, Non Final Office Action mailed Oct. 5, 2009", 8 pgs.
"U.S. Appl. No. 11/490,576, Pre-Appeal Brief Request filed May 12, 2011", 5 pgs.
"U.S. Appl. No. 11/490,576, Response filed Mar. 5, 2010 to Non Final Office Action mailed Oct. 5, 2009", 13 pgs.
"U.S. Appl. No. 11/490,576, Response filed Jun. 17, 2009 to Non Final Office Action mailed Feb. 17, 2009", 13 pgs.
"U.S. Appl. No. 11/490,576, Response filed Oct. 4, 2010 to Non Final Office Action mailed Jul. 12, 2010", 15 pgs.
"U.S. Appl. No. 11/490,576, Response filed Nov. 10, 2010 to Non Final Office Action mailed Jul. 9, 2008", 20 pgs.
"U.S. Appl. No. 11/490,916, Examiner Interview Summary mailed Apr. 12, 2010", 3 pgs.
"U.S. Appl. No. 11/490,916, Examiner Interview Summary mailed Aug. 19, 2009", 2 pgs.
"U.S. Appl. No. 11/490,916, Final Office Action mailed Dec. 17, 2009", 11 pgs.
"U.S. Appl. No. 11/490,916, Non Final OFfice Action mailed May 5, 2009", 10 pgs.
"U.S. Appl. No. 11/490,916, Notice of Allowance mailed Jul. 9, 2010", 4 pgs.
"U.S. Appl. No. 11/490,916, Response filed Jan. 12, 2009 to Restriction Requirement Dec. 11, 2008", 7 pgs.
"U.S. Appl. No. 11/490,916, Response filed Apr. 15, 2010 to Final Office Action mailed Dec. 17, 2009", 12 pgs.
"U.S. Appl. No. 11/490,916, Response filed Sep. 3, 2009 to Non Final Office Action mailed May 5, 2009", 13 pgs.
"U.S. Appl. No. 11/490,916, Restriction Requirement mailed Dec. 11, 2008", 8 pgs.
"U.S. Appl. No. 11/490,916, Supplemental Notice of Allowability Mailed Oct. 14, 2010", 2 pgs.
"U.S. Appl. No. 11/511,152, Final Office Action mailed Aug. 10, 2009", 13 pgs.
"U.S. Appl. No. 11/511,152, Non-Final Office Action mailed Dec. 23, 2008", 14 pgs.
"U.S. Appl. No. 11/511,152, Non-Final Office Action mailed Dec. 30, 2009", 13 pgs.
"U.S. Appl. No. 11/511,152, Notice of Allowance mailed Jul. 28, 2010", 6 pgs.
"U.S. Appl. No. 11/511,152, Preliminary Amendment filed Oct. 17, 2006", 3 pgs.
"U.S. Appl. No. 11/511,152, Response filed Mar. 23, 2009 to Non Final Office Action mailed Dec. 23, 2008", 11 pgs.
"U.S. Appl. No. 11/511,152, Response filed Jun. 30, 2010 to Non Final Office Action mailed Dec. 30, 2009", 12 pgs.
"U.S. Appl. No. 11/511,152, Response filed Nov. 12, 2009 to Final Office Action mailed Aug. 10, 2009", 13 pgs.
"U.S. Appl. No. 11/549,352, Appeal Brief filed Sep. 9, 2009", 36 pgs.
"U.S. Appl. No. 11/549,352, Examiner Interview Summary mailed Jun. 25, 2008", 2 pgs.
"U.S. Appl. No. 11/549,352, Examiner's Answer mailed Nov. 27, 2009 to Appeal Brief filed Sep. 9, 2009", 12 pgs.
"U.S. Appl. No. 11/549,352, Final Office Action mailed Mar. 9, 2009", 10 pgs.
"U.S. Appl. No. 11/549,352, Final Office Action mailed Aug. 26, 2008", 13 pgs.
"U.S. Appl. No. 11/549,352, Non-Final Office Action mailed Feb. 5, 2008", 11 pgs.
"U.S. Appl. No. 11/549,352, Notice of Panel Decision from Pre-Appeal Brief Review mailed Feb. 2, 2009", 2 pgs.
"U.S. Appl. No. 11/549,352, Pre-Appeal Brief for Review filed Dec. 20, 2008", 5 pgs.
"U.S. Appl. No. 11/549,352, Reply Brief filed Jan. 27, 2010", 8 pgs.
"European Application Serial No. 06790023.3, Response filed Aug. 20, 2008 to Office Action mailed Jul. 16, 2008", 17 pgs.
"European Application Serial No. 06790023.3, Response filed Sep. 14, 2009 to Office Action Mailed Mar. 4, 2009", 11 pgs.
"European Application Serial No. 06825988.6, Office Action mailed Jul. 16, 2008", 2 pgs.
"European Application Serial No. 06825988.6, Response filed Aug. 20, 2008 to Office Action mailed Jul. 16, 2008", 26 pgs.
"European Application Serial No. 06825988.6, Response filed Sep. 14, 2009 to Office Action mailed Mar. 4, 2009", 12 pgs.
"International Application Serial No. PCT/US2005/037977, International Preliminary Report on Patentability dated Apr. 24, 2007", 9 pgs.
"International Application Serial No. PCT/US2005/037977, International Search Report mailed Mar. 21, 2006", 4 pgs.
"International Application Serial No. PCT/US2005/037977, Written Opinion mailed Mar. 21, 2006", 8 pgs.
"International Application Serial No. PCT/US2005/037978, International Preliminary Report on Patentability dated Apr. 24, 2007", 13 pgs.
"International Application Serial No. PCT/US2005/037979, International Preliminary Report on Patentability dated Apr. 24, 2007", 9 pgs.
"International Application Serial No. PCT/US2006/033414, International Preliminary Report on Patentability mailed Jun. 19, 2008", 11 pgs.
"International Application Serial No. PCT/US2006/033414, International Search Report mailed Mar. 1, 2007", 5 pgs.

(56) References Cited

OTHER PUBLICATIONS

"International Application Serial No. PCT/US2006/033414, Written Opinion mailed Mar. 1, 2007", 9 pgs.
"International Application Serial No. PCT/2006/040291, International Preliminary Report on Patentability mailed Jun. 19, 2008", 11 pgs.
"International Application Serial No. PCT/US2007/065376, International Preliminary Report on Patentability mailed Oct. 9, 2008", 10 pgs.
"International Application Serial No. PCT/US2007/065376, International Search Report mailed Dec. 14, 2007", 5 pgs.
"International Application Serial No. PCT/US2007/065376, Written Opinion mailed Dec. 14, 2007", 11 pgs.
"International Application Serial No. PCT/US2007/074125, International Preliminary Report on Patentability mailed Feb. 5, 2009", 9 pgs.
"International Application Serial No. PCT/US2007/074125, International Search Report mailed Dec. 6, 2007", 4pgs.
"International Application Serial No. PCT/US2007/074125, Written Opinion mailed Dec. 6, 2007", 8 pgs.
"International Application Serial No. PCT/US2007/074135, International Preliminary Report on Patentability mailed Feb. 5, 2009", 9 pgs.
"International Application Serial No. PCT/US2007/078405, International Preliminary Report on Patentability mailed Mar. 26, 2009", 9 pgs.
"International Application Serial No. PCT/US2009/000693, International Preliminary Report on Patentability mailed Aug. 19, 2010", 9 pgs.
"Japanese Application Serial No. 2007-538087, Office Action mailed Apr. 17, 2012", W/ English Translation, 8 pgs.
"Japanese Application Serial No. 2007-538087, Response filed Mar. 23, 2012 to Office Action mailed Oct. 5, 2011", (W/ English Translation of Claims), 9 pgs.
"Japanese Application Serial No. 2007-538087, Response filed Jul. 13, 2012 to Office Action mailed Apr. 17, 2012", (W/ English Translation of Amended Claims), 13 pgs.
"Japanese Application Serial No. 2007-538088, Response filed Mar. 27, 2012 to Final Office Action mailed Dec. 6, 2011", (W/ English Translation of Claims), 11 pgs.
"Japanese Application Serial No. 2008-544324, Office Action mailed May 22, 2012", (W/ English Translation), 5 pgs.
"Japanese Application Serial No. 2008-544324, Response filed Jan. 27, 2012", (W/ English Translation of Amended Claims), 10 pgs.
"Japanese Application Serial No. 2008-544332, Response filed Mar. 19, 2012 to Office Action mailed Nov. 29, 2011", (W/ English Translation of Claims), 9 pgs.
"Japanese Application Serial No. 2009-503252, Office Action mailed Mar. 21, 2012", (W/ English Translation), 9 pgs.
"Japanese Application Serial No. 2009-503252, Response filed Jun. 20, 2012 to Office Action mailed Mar. 21, 2012", (W/ English Claims), 9 pgs.
"Japanese Application Serial No. 2009-503252, Response filed Oct. 26, 2012 to Office Action mailed Oct. 10, 2012", 7 pgs.
"U.S. Appl. No. 11/549,352, Restriction Requirement mailed Aug. 12, 2013", 5 pgs.
"U.S. Appl. No. 11/683,577, Notice of Allowance mailed Mar. 5, 2013", 11 pgs.
"U.S. Appl. No. 11/854,844, Non Final Office Action mailed Jan. 11, 2013", 15 pgs.
"U.S. Appl. No. 11/854,844, Notice of Allowance mailed Sep. 27, 2013", 9 pgs.
"U.S. Appl. No. 11/854,844, Response filed May 13, 2013 to Non Final Office Action mailed Jan. 11, 2013", 15 pgs.
"U.S. Appl. No. 12/361,884, Notice of Allowance mailed Jan. 17, 2014", 7 pgs.
"U.S. Appl. No. 12/361,884, Notice of Allowance mailed Sep. 25, 2013", 10 pgs.
"U.S. Appl. No. 13/717,027, Preliminary Amendment filed Jun. 25, 2013", 6 pgs.
"U.S. Appl. No. 13/929,286, Non Final Office Action mailed Dec. 11, 2013", 15 pgs.
"U.S. Appl. No. 13/929,286, Preliminary Amendment filed", 7 pgs.
"U.S. Appl. No. 14/044,094, Non Final Office Action mailed Jan. 17, 2014", 19 pgs.
"U.S. Appl. No. 14/044,094, Preliminary Amendment filed Oct. 28, 2013", 8 pgs.
"International Application Serial No. PCT/US2005/037979, International Search Report mailed Mar. 21, 2006" 4 pgs.
"International Application Serial No. PCT/US2005/037979, Written Opinion mailed Mar. 21, 2006", 8 pgs.
"International Application Serial No. PCT/US2006/040291, Search Report mailed Apr. 4, 2006", 5 pgs.
"International Application Serial No. PCT/US2006/040291, Written Opinion mailed Apr. 4, 2007", 9 pgs.
"International Application Serial No. PCT/US2007/074315, International Search Report mailed Nov. 6, 2007" 4 pgs.
"International Application Serial No. PCT/US2007/074315, Written Opinion mailed Nov. 6, 2007" 8 pgs.
"International Application Serial No. PCT/US2007/078405, International Search Report mailed May 20, 2008", p. 220, 7 pgs.
"International Application Serial No. PCT/US2007/078405,Written Opinion mailed May 20, 2008", p. 237, 7 pgs.
"International Application Serial No. PCT/US2009/000587, International Search Report mailed Apr. 24, 2009", 7 pgs.
"International Application Serial No. PCT/US2009/000587, Written Opinion mailed Apr. 24, 2009", 8 pgs.
"International Application Serial No. PCT/US2009/000693, International Search Report mailed May 8, 2009", 5 pgs.
"International Application Serial No. PCT/US2009/000693, Written Opinion mailed May 8, 2009", 8 pgs.
"Japanese Application Serial No. 2007-538087, Office Action mailed Apr. 11, 2011", (W/ English Translation), 5 pgs.
"Japanese Application Serial No. 2007-538087, Office Action mailed Oct. 5, 2011", (W/ English Translation), 14 pgs.
"Japanese Application Serial No. 2007-538087, Response filed Jun. 27, 2011 to Office Action dated Apr. 11, 2011", (W/ English Translation of Amended Claims), 12 pgs.
"Japanese Application Serial No. 2007-538088, Notice of Final Rejection mailed Dec. 6, 2011", (W/ English Translation), 9 pgs.
"Japanese Application Serial No. 2007-538088, Office Action mailed Jun. 13, 2011", (W/ English Translation), 5 pgs.
"Japanese Application Serial No. 2007-538088, Response filed Aug. 25, 2011 to Office Action dated Jun. 13, 2011" (W/ English Translation of Amended Claims), 9 pgs.
"Japanese Application Serial No. 2007-538089, Office Action mailed Mar. 3, 2011", (W/ English Translation), 6 pgs.
"Japanese Application Serial No. 2007-538089, Response filed May 25, 2011 to Office Action mailed Mar. 3, 2011", (W/ English Translation of Amended Claims), 8 pgs.
"Japanese Application Serial No. 2008-544324, Office Action mailed Nov. 22, 2011", (W/ English Translation), 5 pgs.
"Japanese Application Serial No. 2008544332, Office Action mailed Nov. 29, 2011", (W/ English Translation), 5 pgs.
"Telemetry Research Transcutaneous Energy Transfer (TET) Technology Summary", Telemetry Research Ltd., www.telemetryresearch.com, (No date listed), 1 pg.
Busch, M., et al., "On the Heating of Inductively Coupled Resonators (Stents) During MRI Examination", Magnetic Resonance in Medicine, 54, (2005), 775-785.
Manoharan, G., et al., "Novel Passive Implantable atrial defibrillator using transcutaneous radiofrequency energy transmission successfully cardioverts atrial fibrillation", Circulation, 108(11), (Sep. 16, 2003), 1382-8.
Piella, J. P., "Energy management, wireless and system solutions for highly integrated implantable devices", Doctoral Thesis by Jordi Parramon I Piella for the Universitat Autonoma de Barcelona, certified Dec. 2001, 62 pgs.
Si, Ping, et al., "A Frequency Control Method for Regulating Wireless Power to Implantable Devices", IEEE Transactions on Biomedical Circuits and Systems, 2(1), (Mar. 2008), 22-29.
Swain, E., "Breakthrough Products Could put Lesser-Known Firms on the map", MDDI, (Apr. 2004), 6 pgs.

(56) References Cited

OTHER PUBLICATIONS

Wagner, Brian K. "Electrodes, Leads, and Biocompatibility", Chapter 6—Design of Cardiac Pacemakers, edited by John G. Webster., (1995), 133-160.
"U.S. Appl. No. 11/394,601, Response filed May 4, 2009 to Restriction Requirement mailed Apr. 2, 2009", 9 pgs.
"U.S. Appl. No. 11/490,576, Notice of Allowance mailed Jun. 4, 2012", 8 pgs.
"U.S. Appl. No. 11/490,576, Response filed Apr. 9, 2012 to Non Final Office Action mailed No. 9, 2011", 11 pgs.
"U.S. Appl. No. 11/683,584, Notice of Allowance mailed Aug. 7, 2012", 6 pgs.
"U.S. Appl. No. 11/745,105, Non Final Office Action mailed Feb. 7, 2012", 12 pgs.
"U.S. Appl. No. 11/745,105, Notice of Allowance mailed Aug. 20, 2012", 5 pgs.
"U.S. Appl. No. 11/745,105, Response filed Aug. 6, 2012 to Non Final Office Action mailed Feb. 7, 2012", 11 pgs.
"U.S. Appl. No. 12/361,884, Advisory Action mailed Sep. 10, 2012", 3 pgs.
"U.S. Appl. No. 12/361,884, Examiners Interview Summary mailed Oct. 1, 2012", 3 pgs.
"U.S. Appl. No. 12/361,884, Final Office Action mailed Jul. 3, 2012", 17 pgs.
"U.S. Appl. No. 12/361,884, Response filed Apr. 12, 2012 to Non Final Office Action mailed Oct. 12, 2011", 21 pgs.
"U.S. Appl. No. 12/361,884, Response filed Aug. 28, 2012 to Final Office Action mailed Jul. 3, 2012", 18 pgs.
"U.S. Appl. No. 12/361,884, Response filed Oct. 3, 2012 to Final Office Action mailed Jul. 3, 2012", 18 pgs.
"U.S. Appl. No. 12/365,428, Notice of Allowance mailed Feb. 22, 2012", 7 pgs.
"U.S. Appl. No. 12/365,428, Response filed Jan. 31, 2012 to Non Final Office Action mailed Aug. 31, 2011", 15 pgs.
"U.S. Appl. No. 11/549, 352, Appeal Decision mailed Jul. 17, 2012", 9 pgs.
"European Application Serial No. 05815206.7, Office Action mailed May 16, 2012". 4 pgs.
"European Application Serial No. 05815206.7, Office Action mailed Sep. 12, 2012", 27 pgs.
"European Application Serial No. 05817448.3, Office Action mailed May 16, 2012", 5 pgs.
"European Application Serial No. 05817448.3, Response filed Sep. 14, 2012 to Office Action mailed May 16, 2012", 14 pgs.
"European Application Serial No. 06790023.3, Office Action mailed Jul. 16, 2008", 2 pgs.
"U.S. Appl. No. 10/971,550, 312 Amendment filed Mar. 20, 2009", 6 pgs.
"U.S. Appl. No. 10/971,550, Examiner Interview Summary mailed Jan. 22, 2008", 4 pgs.
"U.S. Appl. No. 10/971,550, Non Final Office Action mailed Mar. 19, 2007", 11 pgs.
"U.S. Appl. No. 10/971,550, Non-Final Office Action mailed Nov. 5, 2007", 19 pgs.
"U.S. Appl. No. 10/971,550, Notice of Allowance mailed Jul. 14, 2008", 4 pgs.
"U.S. Appl. No. 10/971,550, Notice of Allowance mailed Dec. 22, 2008" 4 pgs.
"U.S. Appl. No. 10/971,550, PTO Response to 312 Amendment mailed Apr. 6, 2009", 2 pgs.
"U.S. Appl. No. 10/971,550, Response filed Feb. 22, 2007 to Restriction Requirement mailed Jan. 22, 2007", 1 pg.
"U.S. Appl. No. 10/971,500, Response filed Mar. 25, 2008 to Non Final Office Action mailed Nov. 5, 2007", 17 pgs.
"U.S. Appl. No. 10/971,550, Response filed Sep. 4, 2007 to Non-Final Office Action mailed Mar. 19, 2007", 15 pgs.
"U.S. Appl. No. 10/971,550, Restriction Requirement mailed Jan. 22, 2007", 22 pgs.
"U.S. Appl. No. 11/075,375, Restriction Requirement mailed Apr. 10, 2007", 6 pgs.
"U.S. Appl. No. 11/075,375, Examiner Interview Summary mailed Jan. 12, 2009", 4 pgs.
"U.S. Appl. No. 11/075,375, Examiner Interview Summary mailed May 1, 2008", 4 pgs.
"U.S. Appl. No. 11/075,375, Final Office Action mailed Jan. 23, 2009", 10 pgs.
"U.S. Appl. No. 11/075,375, Final Office Action mailed Apr. 16, 2009", 10 pgs.
"U.S. Appl. No. 11/075,375, Non-Final Office Action mailed Jun. 8, 2007", 11 pgs.
"U.S. Appl. No. 11/075,375, Non-Final Office Action mailed Aug. 11, 2008", 15 pgs.
"U.S. Appl. No. 11/075,375, Notice of Allowance mailed Sep. 4, 2009", 6 pgs.
"U.S. Appl. No. 11/075,375, Response filed Jan. 12, 2009 to Non-Final Office Action mailed Aug. 11, 2008", 18 pgs.
"U.S. Appl. No. 11/075,375, Response filed May 7, 2007 to Restriction Requirement mailed Apr. 10, 2007", 8 pgs.
"U.S. Appl. No. 11/075,375, Response filed May 22, 2008 to Final Office Action mailed Jan. 23, 2008", 16 pgs.
"U.S. Appl. No. 11/075,375, Response filed Jul. 16, 2009 to Final Office Action mailed Apr. 16, 2009", 13 pgs.
"U.S. Appl. No. 11/075,375, Response filed Oct. 26, 2007 to Non-Final Office Action mailed Jun, 8, 2007", 10 pgs.
"U.S. Appl. No. 11/075,376, Final Office Action mailed Jan. 7, 2008", 11 pgs.
"U.S. Appl. No. 11/075,376, Non-Final Office Action mailed Jun. 26, 2007", 9 pgs.
"U.S. Appl. No. 11/075,376, Non-Final Office Action mailed Aug. 20, 2008", 16 pgs.
"U.S. Appl. No. 11/075,376, Restriction Requirement mailed Apr. 10, 2007", 6 pgs.
"U.S. Appl. No. 11/075,376, Examiner Interview Summary mailed Jan. 12, 2009", 4 pgs.
"U.S. Appl. No. 11/075,376, Examiner Interview Summary mailed Apr. 2, 2008", 4 pgs.
"U.S. Appl. No. 11/075,376, Final Office Action mailed Apr. 8, 2009", 17 pgs.
"U.S. Appl. No. 11/075,376, Notice of Allowance mailed Aug. 24, 2009", 6 pgs.
"U.S. Appl. No. 11/075,376, Response filed Jan. 21, 2009 to Non-Final Office Action mailed Aug. 20, 2008", 22 pgs.
"U.S. Appl. No. 11/075,376, Response filed May. 7, 2007 to Restriction Requirement mailed Apr. 10, 2007", 10 pgs.
"U.S. Appl. No. 11/075,376, Response filed May 7, 2007 to Restriction Requirement mailed Apr. 10, 2007", 8 pgs.
"U.S. Appl. No. 11/075,376, Response filed Jun. 9, 2008 to Final Office Action mailed Jan. 7, 2008", 20 pgs.
"U.S. Appl. No. 11/075,376, Response filed Jul. 8, 2009 to Final Office Action mailed Apr. 8, 2009", 11 pgs.
"U.S. Appl. No. 11/075,376, Response filed Oct. 26, 2007 to Non-Final Office Action mailed Jun. 26, 2007", 14 pgs.
"U.S. Appl. No. 11/316,120, Final Office Action mailed Aug. 20, 2008", 9 pgs.
"U.S. Appl. No. 11/316,120, Non-Final Office Action mailed Apr. 17, 2009", 8 pgs.
"U.S. Appl. No. 11/316,120, Decision on Pre-Appeal Brief Request mailed Apr. 19, 2011", 2 pgs.
"U.S. Appl. No. 11/316,120, Final Office Action mailed Oct. 28, 2010", 8 pgs.
"U.S. Appl. No. 11/316,120, Final Office Action mailed Nov. 12, 2009", 8 pgs.
"U.S. Appl. No. 11/316,120, Non Final Office Action mailed Apr. 11, 2008", 7 pgs.
"U.S. Appl. No. 11/316,120, Non-Final Office Action mailed May 27, 2010", 7 pgs.
"U.S. Appl. No. 11/316,120, Notice of Allowance mailed Jul. 20, 2011", 7 pgs.
"U.S. Appl. No. 11/316,120, Pre-Appeal Brief Request filed Mar. 25, 2011", 5 pgs.
"U.S. Appl. No. 11/316,120, Response filed Mar. 25, 2011 to Final Office Action mailed Oct. 28, 2010", 8 pgs.

(56) References Cited

OTHER PUBLICATIONS

"U.S. Appl. No. 11/316,120, Response filed Apr. 12, 2010 to Final Office Action mailed Nov. 12, 2009", 12 pgs.
"U.S. Appl. No. 11/316,120, Response filed May 14, 2008 to Non Final Office Action mailed Apr. 11, 2008", 12 pgs.
"U.S. Appl. No. 11/549,352, Response Filed Jul. 7, 2008 to Non-Final Office Action mailed Feb. 5, 2008", 17 pgs.
"U.S. Appl. No. 11/683,577, Examiner Interview Summary mailed Jul. 7, 2008", 4 pgs.
"U.S. Appl. No. 11/683,577, Final Office Action mailed Nov. 9, 2009", 14 pgs.
"U.S. Appl. No. 11/683,577, Non Final Office Action mailed Mar. 5, 2009", 13 pgs.
"U.S. Appl. No. 11/683,577, Response filed May 7, 2010 to Final Office Action mailed Nov. 9, 2009", 14 pgs.
"U.S. Appl. No. 11/683,577, Response filed Aug. 5, 2009 to Non Final Office Action mailed Mar. 5, 2009", 10 pgs.
"U.S. Appl. No. 11/683,584, Non-Final Office Action mailed Apr. 1, 2009", 9 pgs.
"U.S. Appl. No. 11/683,584, Examiner Interview Summary mailed Jul. 7, 2009", 4 pgs.
"U.S. Appl. No. 11/683,584, Final Office Action mailed Jan. 29, 2010", 9 pgs.
"U.S. Appl. No. 11/683,584, Preliminary Amendment filed Mar. 8, 2007", 1 pgs.
"U.S. Appl. No. 11/683,584, Response filed Jul. 1, 2009 to Non Final Office Action mailed Apr. 1, 2009", 7 pgs.
"U.S. Appl. No. 11/683,584, Response filed Jul. 21, 2010 to Final Office Action mailed Jan. 29, 2010", 12 pgs.
"U.S. Appl. No. 11/745,070, Final Office Action mailed Dec. 11, 2009", 18 pgs.
"U.S. Appl. No. 11/745,070, Non Final Office Action mailed Apr. 27, 2009", 11 pgs.
"U.S. Appl. No. 11/745,070, Response filed Jul. 27, 2009 to Non Final Office Action mailed Apr. 27, 2009", 11 pgs.
"U.S. Appl. No. 11/745,105, Final Office Action mailed Mar. 30, 2010", 9 pgs.
"U.S. Appl. No. 11/745,105, Non Final Office Action mailed May 11, 2011", 13 pgs.
"U.S. Appl. No. 11/745,105, Non Final Office Action mailed Sep. 18, 2009", 9 pgs.
"U.S. Appl. No. 11/745,105, Notice of Allowance mailed Oct. 31, 2011", 5 pgs.
"U.S. Appl. No. 11/745,105, Response filed Jan. 19, 2010 to Non Final Office Action mailed Sep. 18, 2009", 12 pgs.
"U.S. Appl. No. 11/745,105, Response filed Jun. 22, 2009 to Restriction Requirement mailed May 21, 2009", 6 pgs.
"U.S. Appl. No. 11/745,105, Response filed Jul. 29, 2010 to Final Office Action mailed Mar. 30, 2010", 12 pgs.
"U.S. Appl. No. 11/745,105, Response filed Sep. 12, 2011 to Non Final Office Action mailed May 11, 2011", 13 pgs.
"U.S. Appl. No. 11/745,105, Restriction Requirement mailed May 21, 2009", 6 pgs.
"U.S. Appl. No. 12/361,884, Non Final Office Action mailed Oct. 12, 2011", 16 pgs.
"U.S. Appl. No. 12/361,884, Preliminary Amendment filed Jun. 30, 2011", 12 pgs.
"U.S. Appl. No. 12/361,884,Supplemental Preliminary Amendment filed Jul. 27, 2011", 12 pgs.
"U.S. Appl. No. 12/365,428, Non Final Office Action mailed Aug. 31, 2011", 9 pgs.
"U.S. Appl. No. 12/910,106, Non Final Office Action mailed Apr. 4, 2011", 9 pgs.
"U.S. Appl. No. 12/910,106, Notice of Allowance mailed Jan. 26, 2012", 6 pgs.
"U.S. Appl. No. 12/910,106,Notice of Allowance mailed Oct. 27, 2011", 5 pgs.
"U.S. Appl. No. 12/910,106, Response filed Aug. 2, 2011 to Non-Final Office Action mail Apr. 4, 2011", 14 pgs.
"European Application Serial No. 05815206.7, Response filed Apr. 19, 2010 to Communication Dec. 18, 2009", 27 pgs.
"European Application Serial No. 05815206.7, Communication mailed Dec. 18, 2009", 27 pgs.
"European Application Serial No. 05815215.8, Communication mailed Dec. 18, 2009", 2 pgs.
"European Application Serial No. 05815215.8, Response filed Mar. 19, 2010 to Communication mailed Dec. 18, 2009", 12 pgs.
"European Application Serial No. 058174483, Communication mailed Dec. 18, 2009" 2 pgs.
"European Application Serial No. 05817448.3, Response filed Mar. 19, 2010 to Communication mailed Dec. 18, 2009" 2 pgs.
"European Application Serial No. 06790023.3, Office Action mailed Mar. 4, 2009", 7 pgs.
"European Application Serial No. 06825988.6, Office Action mailed Mar. 4, 2009", 7 pgs.
"European Application Serial No. 06847612.6, Office Action mailed May 26, 2009", 3 pgs.
"European Application Serial No. 07759589.0, Office Action mailed Jan. 29, 2009", 3 pgs.
"European Application Serial No. 07759589.0 Office Action mailed Feb. 18, 2010", 3 pgs.
"European Application Serial No. 07759589.0, Response filed Jun. 5, 2009 to Office Action mailed Jan. 29, 2009", 6 pgs.
"European Application Serial No. 07759589.0, Response filed Jun. 24, 2010 to Office Action mailed Feb. 18, 2010", 6 pgs., 2009, 6 pgs.
"European Application Serial No. 07759589.0, Summons to Attend Oral Proceedings dated May 17, 2011", 3 pgs.
"European Application Serial No. 07759589.0, Written Submission filed Dec. 5, 2011 to Summons to Attend Oral Proceedings dated May 17, 2011", 16 pgs.
"International Application Serial No. PCT/US2005/037978, International Search Report mailed Jun. 13, 2006", 5 pgs.
"International Application Serial No. PCT/US2005/037978, Written Opinion mailed Jun. 13, 2006", 5 pgs.

US 9,662,487 B2

DELIVERY OF CARDIAC STIMULATION DEVICES

CROSS-REFERENCE TO RELATED APPLICATIONS

This application is a Continuation of U.S. application Ser. No. 13/476,599, filed May 21, 2012, which is a Continuation of U.S. application Ser. No. 12/910,106, filed on Oct. 22, 2010, now issued as U.S. Pat. No. 8,185,213, which is a Division of U.S. application Ser. No. 11/490,916, filed Jul. 21, 2006, now issued as U.S. Pat. No. 7,840,281, the benefit of priority of each of which is claimed herein, and each of which is hereby incorporated herein by reference in its respective entirety.

TECHNICAL FIELD

This document relates to systems that electrically stimulate cardiac or other tissue and to systems for delivering stimulation devices.

BACKGROUND

Pacing instruments can be used to treat patients suffering from any of a number of heart conditions, such as a reduced ability to deliver sufficient amounts of blood from the heart. For example, some heart conditions may cause or be caused by conduction defects in the heart. These conduction defects may lead to irregular or ineffective heart contractions. Cardiac pacing systems (e.g., a pacemaker or an implantable defibrillator with pacing capability) may be implanted in a patient's body so that wire electrodes in contact with the heart tissue provide electrical stimulation to regulate electrical conduction in the heart tissue. Such regulated electrical stimulation is done to cause the heart to contract and hence pump blood.

The wired pacing systems in current use include a pulse generator that is implanted, typically in a patient's pectoral region just under the skin. One or more wired leads extend from the pulse generator so as to contact various portions of the heart. An electrode at a distal end of a lead may provide the electrical contact to the heart for delivery of the electrical pulses generated by the pulse generator and delivered to the electrode through the lead.

The use of wired leads may limit the number of sites of heart tissue at which electrical energy may be delivered. For example, most commercially available pacing leads are not indicated for use inside the left chambers of the heart. One reason is that the high pumping pressure in the left chambers of the heart may cause a thrombus or clot that forms on the bulky wired lead to eject into distal arteries, thereby causing stroke or other embolic injury. Thus, in order to pace the left side of the heart with a wired lead, most wired leads are directed through the cardiac venous system (outside the left chambers of the heart) to a site in a cardiac vein along the exterior of the left side of the heart.

In one example of a pacing therapy that includes pacing of a left heart chamber, a treatment known as biventricular pacing may be performed when the left ventricle does not contract in synchrony with the right ventricle. In order to perform such pacing therapy, typically a first wired lead is implanted through a vein into the right atrium, a second wired lead is implanted through a vein into the right ventricle, and a third wired lead is implanted through a vein and into the coronary sinus vein (to pace the left ventricle wall from outside the left ventricle). These three wired leads may be connected to a pacemaker device (e.g., implanted in the pectoral region) in an attempt to regulate the contractions of the right and left ventricles.

In addition to conventional wired pacing systems, one type of pacing system being developed includes wireless operation. For example, some pacing systems may use wireless electrodes that are attached to the outer epicardial surface of the heart (external to the heart chambers) or embedded in a cardiac vein (external to the heart chambers) to stimulate heart tissue.

SUMMARY

Some embodiments of an electrical stimulation system employ wireless electrode assemblies to provide pacing therapy, defibrillation therapy, or other stimulation therapy. The wireless electrode assemblies may receive energy via an inductive coupling with another device outside the heart (e.g., implanted adjacent to one or more ribs) so as to provide electrical stimulation to the nearby heart tissue. In certain embodiments, the wireless electrode assemblies may include a guide wire channel so that each electrode assembly can be advanced over a guide wire instrument through the endocardium. For example, a distal tip portion of a guide wire instrument can penetrate through the endocardium and into the myocardial wall of a heart chamber, and the electrode assembly may then be advanced over the guide wire and into the heart chamber wall. In such circumstances, the guide wire instrument (and other portions of the delivery system) can be retracted from the heart chamber wall, thereby leaving the electrode assembly embedded in the heart tissue.

Some embodiments include an electrode delivery system for delivering a wireless electrode assembly into a heart chamber wall. The system may include a wireless electrode assembly including a body that defines a guide wire channel extending therethrough. The system may also include a delivery catheter to direct the wireless electrode assembly through a heart chamber and toward a heart chamber wall. The delivery catheter may have a distal opening through which the wireless electrode assembly is passable for delivery into the heart chamber wall. The system may further include a guide wire instrument passable through the delivery catheter to penetrate into the heart chamber wall. The guide wire instrument may have a distal tip portion that is slidable within the guide wire channel of the wireless electrode assembly when the wireless electrode assembly is advanced over the guide wire instrument into the heart chamber wall.

In particular embodiments, an electrode delivery system for delivering a wireless electrode assembly may include a delivery catheter to direct a wireless electrode assembly toward a heart chamber wall when the electrode assembly is disposed therein. The delivery catheter may have a distal opening through which the wireless electrode assembly is passable. The system may also include an actuation member to push the electrode assembly out of the distal opening of the delivery catheter and into the heart chamber wall. The actuation member may be movably adjustable within the delivery catheter. Further, the system may include a guide wire instrument passable through the delivery catheter and having a distal tip portion to define a penetration path through endocardium tissue and into myocardium tissue of the heart wall chamber. When the actuation member pushes the electrode assembly out of the distal opening of the delivery catheter, the electrode assembly advances over the distal tip portion of the guide wire instrument to implant into the myocardium tissue along the penetration path.

In some embodiments, a wireless electrode assembly for electrical stimulation of heart tissue may include a body portion at least partially containing a circuit to deliver electrical stimulation from an electrode surface. The assembly may also include a tissue penetration surface along the body portion to initiate penetration of the body portion into a heart chamber wall. The assembly may further include a guide wire channel defined by the body portion and extending in a longitudinal direction through the body portion toward the tissue penetration surface.

Some embodiments include a method for delivering a wireless electrode assembly into a heart chamber wall. The method may include directing a distal portion of a delivery catheter into a heart chamber, and advancing a guide wire instrument out of the distal portion of the delivery catheter to penetrate a distal tip portion of guide wire instrument into a heart chamber wall. The method may also include advancing a wireless electrode assembly out of the distal portion of the delivery catheter and over the distal tip portion of the guide wire instrument to implant the electrode assembly in the heart chamber wall.

Some of the embodiments described herein may have one or more of the following advantages. First, the delivery system may include a guide wire instrument that initiates penetration of the heart chamber wall, thereby facilitating the subsequent penetration by the electrode assembly. Second, the guide wire instrument may include one or more sensor electrodes to sense local electrical activity (e.g., an electrogram or the like) and to transmit a test stimulation signal (e.g., a pacing signal) at the proposed implantation site. Third, the delivery system may be configured to advance the electrode assembly in a controlled manner to a selected insertion depth into the heart wall tissue. Fourth, the delivery system may include a magnetic coupling device that releasably retains the electrode assembly in a delivery catheter. Fifth, the delivery system may include a guide wire instrument that is configured to guide the electrode assembly into the heart wall tissue along a curved insertion path, thereby permitting the electrode assembly to be embedded between selected tissue fibers. Sixth, the delivery system may include a guide wire instrument having one or more fixation devices extending therefrom so as to secure the guide wire instrument to the heart wall tissue and maintain the guide wire position during the implantation process. Seventh, the delivery system may include a guide wire instrument having a detachable tip portion that serves to reduce migration and to maintain the orientation of the electrode assembly implanted in the heart wall tissue. Eighth, the delivery system may include a delivery catheter that is releasably attachable to the heart chamber wall so as to maintain the position of the delivery catheter during the implantation process.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
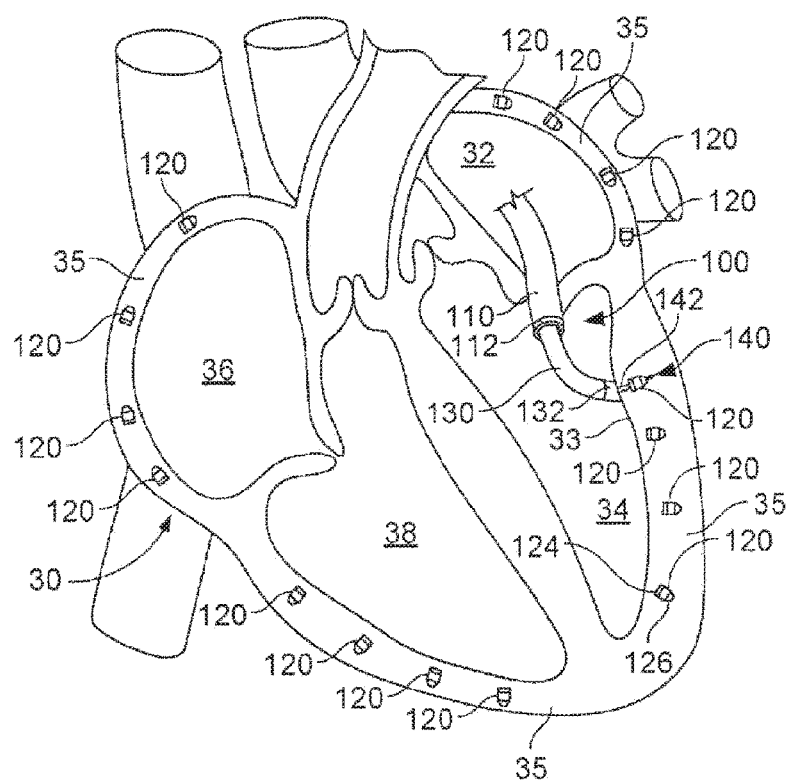
FIG. 1 is a section view of a heart and at least a portion of an electrode delivery system, in accordance with some embodiments.

Referring to FIG. 1, an electrode delivery system 100 may be used to introduce one or more wireless electrode assemblies 120 into the heart chamber walls. In this example, there are four wireless electrode assemblies 120 implanted in the heart chamber wall of each of the left atrium 32, the left ventricle 34, the right atrium 36, and the right ventricle 38. As described below in connection with FIGS. 3-5, the wireless electrode assemblies 120 may be part of an electrical stimulation system 20 that wirelessly transmits energy to the electrode assemblies 120 for electrical stimulation of the surrounding heart wall tissue 35. The electrode delivery system 100 includes a delivery catheter 130 with a distal opening and a guide wire instrument 140 that is passable through the delivery catheter 130. The guide wire instrument 140 is capable of penetrating into a heart chamber wall, as shown in FIG. 1. After penetration, an electrode assembly 120 is advanced in a distal direction over at least a portion of the guide wire instrument 140 so that the electrode assembly 120 is implanted entirely within the heart chamber wall, as shown in FIG. 1. Exemplary embodiments of the proximal portions of the delivery catheter 130 and the guide wire 140 extending outside the patient's body are shown and described below in connection with FIG. 3.

In more detail, the delivery system 100 shown in FIG. 1 includes a guide sheath 110 that is capable of being directed (e.g., by a surgeon or other user) through one or more veins or arteries to the targeted chamber of the heart 30 (e.g., the left ventricle 34 is the targeted chamber in the embodiment shown in FIG. 1). For example, in those embodiments in which the atrial septum or a heart valve is to be crossed during the delivery procedure, the guide sheath 110 can maintain such a crossing while a plurality of electrode assemblies 120 are directed therethrough into the targeted heart chamber. For example, in the embodiment shown in FIG. 1, the guide sheath 110 maintains a crossing through the atrial septum (e.g., entering through the right atrium 36, passing through the atrial septum, and passing into the left atrium 32) and maintain a crossing through the left mitral valve (e.g., passing through the left mitral valve, and passing into the left ventricle 34). In an alternative example, the guide sheath 110 can be directed through a femoral artery, around the aortic arch, and into the left ventricle 34.

After the guide sheath 110 is deployed into the targeted heart chamber, multiple wireless electrode assemblies 120 may be consecutively delivered through the guide sheath 110 using at least one delivery catheter 130. The multiple assemblies 120 may be delivered without having to remove the outer sheath 110, thereby reducing the delivery time and reducing the likelihood of trauma to the atrial septum or heart valve crossing due to repeated insertions.

Still referring to FIG. 1, the guide wire instrument 140 has a distal tip adapted to penetrate through the endocardium 33 and into the heart wall tissue 35 (e.g., tissue such as the myocardial wall) before the electrode assembly 120 is advanced into the heart wall tissue 35. As such, the guide wire instrument 140 may initiate a penetration path into the heart chamber wall, thereby facilitating the subsequent penetration by the electrode assembly 120 along the penetration path. For example, in the embodiment depicted in FIG. 1, the distal tip portion 142 of the guide wire instrument 140 can penetrate through the endocardium 33 and into the heart wall tissue 35, thereby forming an opening in the endocardium 33. Then the electrode assembly 120 can be advanced over the distal tip portion 142 to further dilate opening in the endocardium 33 (which was previously formed by the guide wire instrument 140) and to penetrate into the heart wall tissue 35.

In addition, the guide wire instrument 140 may include at least one sensor electrode 144 (FIG. 2) along its distal tip portion 142 that is configured to sense local electrical activity (e.g., an electrogram or the like) and to transmit a test stimulation signal (e.g., a pacing signal) after initiating the penetration into the implantation site. In these circumstances, the guide wire instrument 140 may be used to determine if the implantation site is suitable for receipt of an electrode assembly 120 before the electrode assembly 120 is advanced into the heart wall tissue 35. For example, the guide wire instrument 140 may comprise a conductive electrical line extending from the sensor electrode 144 (FIG. 2) along the distal tip portion 142 to the proximal portion 148 (FIG. 3) of the guide wire instrument 140 (e.g., outside the patient's body). In these circumstances, the guide wire instrument 140 may be connected to an electrogram or ECG monitor system or the like so that a physician may view the local electrical activity in the heart wall tissue 35 into which the distal tip portion 142 has penetrated. Further, a pulse generator device or the like may be electrically connected to the proximal portion 148 (FIG. 3) of the guide wire instrument 140 (e.g., outside the patient's body) so as to transmit test pacing signals to heart wall tissue 35 adjacent to the distal tip portion 142. In some circumstances, the sensor electrode 144 may comprise a marker material that permits viewability of the guide wire instrument 140 in the heart 30 using medical imaging techniques. In addition or in the alternative, at least the distal tip portion 142 of the guide wire instrument 140 may comprise a marker material or a marker band (not shown) to permit viewability of the guide wire instrument 140 in the heart 30 using medical imaging techniques.

Figure 2:
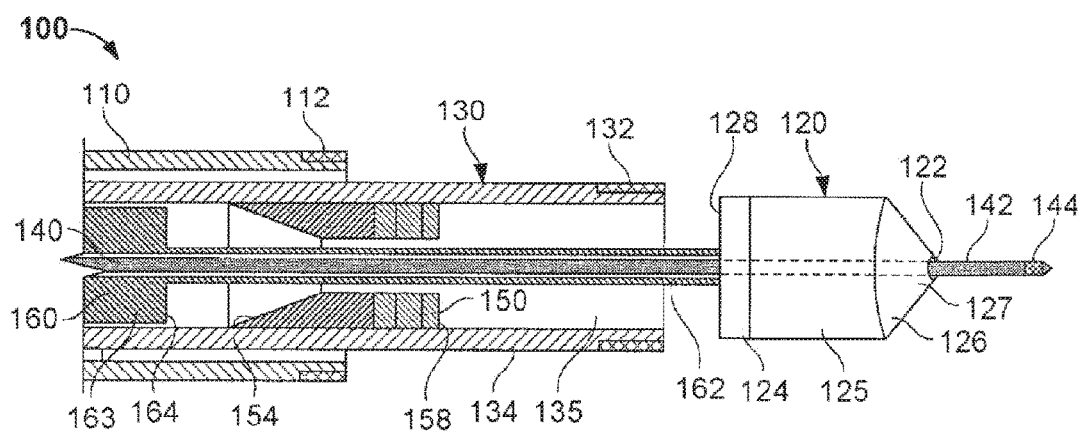
FIG. 2 is a partial cross-sectional view of the portion of the electrode delivery system of FIG. 1.

FIG. 2 shows a more detailed view of the distal portion of the embodiments of the delivery system 100 and the wireless electrode assembly 120 previously described in connection with FIG. 1. The electrode assembly 120, in this example, includes a guide wire channel 122 through which at least a distal tip portion 142 of the guide wire instrument 140 extends. A movable engagement between the electrode assembly 120 and the guide wire instrument 140 (e.g., a slidable engagement) permits the electrode assembly 120 to be advanced over the guide wire instrument 140 into the heart wall tissue 35 and permits the guide wire instrument 140 (and other portions of the delivery system 100) to be retracted from the electrode assembly 120 after implantation is completed. In this embodiment, the electrode assembly 120 also includes a body portion 125 that at least partially contains a circuit (described in more detail below in connection with FIG. 5) to deliver electrical stimulation from one or more electrode surfaces 124 and 126. For example, in those embodiments in which the electrode assembly 120 provides bipolar functionality, the electrode assembly 120 may include a first electrode 124 disposed opposite a second electrode 126 so as to provide a stimulation circuit from one electrode (e.g., the second electrode 126), through the surrounding heart wall tissue 35, and to the other electrode (e.g., the first electrode 124). As shown in FIG. 2, the first and second electrodes 124 and 126 may be disposed along an outer surface of the body portion 125 so as to contact the heart wall tissue 35 when implanted therein. The electrode assembly 120 may also include a tissue penetration surface 127 along the body portion 125 to facilitate penetration of the body portion 125 into the heart wall tissue 35. For example, the tissue penetration surface 127 has a generally conical shape or other distally narrowing shape to facilitate the insertion process. In the embodiment depicted in FIG. 2, the distal electrode 126 extends along the conical surface of the tissue penetration surface 127. The guide wire channel 122 may extend in a substantially longitudinal direction through the body portion 125 toward the tissue penetration surface 127 so that the tissue penetration surface 127 can be advanced in the direction of the previously inserted guide wire instrument 140. As previously described, in this embodiment, the guide wire instrument 140 includes at least one sensor electrode 144 disposed along the distal tip portion 142 to sense local electrical activity (e.g., an electrogram or the like) and to transmit a test stimulation signal (e.g., a pacing signal).

In some embodiments, the wireless electrode assemblies 120 may be sized to be implanted entirely within a heart chamber wall, which can have a wall thickness of about 3 mm to about 30 mm and more specifically about 5 mm to about 25 mm for ventricle walls, and about 1 mm to about 5 mm and more specifically about 2 mm to about 4 mm for atrial walls. Also in these embodiments, the wireless electrode assemblies 120 are sized to slidably receive at least the distal tip portion 142 of the guide wire instrument 140, which can have an outer diameter of about 0.1 mm to about 1.0 mm, about 0.2 mm to about 0.8 mm, and more specifically about 0.25 mm to about 0.5 mm. Accordingly, in such embodiments, the body portion 125 of the electrode assembly 120 may have a longitudinal length of about 20 mm or less, about 15 mm or less, about 10 mm or less, for example, about 3 mm to about 10 mm, and in some circumstances (e.g., implantation in the atrial wall) about 5 mm or less, for example about 3 mm to about 5 mm. Also, in these embodiments, the body portion 125 may have a generally circular cross-sectional shape with a maximum outer diameter of about 0.5 mm to about 3.5 mm, about 1 mm to about 3 mm, and more specifically about 1.5 mm to about 2.5 mm. Further, in some embodiments, the guide wire channel 122 may have a diameter of about 0.15 mm to about 1.05 mm, about 0.25 mm to about 0.85 mm, and about 0.30 mm to about 0.55 mm so as to accommodate the guide wire instrument 140 having a diameter as previously described.

Still referring to FIG. 2, the electrode assembly 120 may be releasably retained in the distal portion 134 of the delivery catheter 130 during advancement through the guide sheath 110. In this embodiment, a magnetic coupling device 150 is disposed in the distal portion 134 of the delivery catheter 130 so as to releasably retain the electrode assembly 120 in a non-deployed position (not shown in FIG. 2). For example, the magnetic coupling device 150 may include one or more ring magnets axially aligned with the distal portion 134 of the delivery catheter 130 so that a distal surface 158 of the magnetic coupling device 150 is magnetically attracted to an opposing surface 128 of the electrode assembly 120. In this embodiment, the magnetic coupling device 150 comprises rare earth magnets and the proximal surface 128 of the electrode assembly 120 may comprise a magnetically attractable metal material, such as stainless steel or the like. In some circumstances, the magnetic coupling device 150 disposed in the distal portion 134 of the delivery catheter 130 may aid in controlled-delivery of the delivery catheter through the patient's body and into the targeted heart chamber. For example, the magnetic coupling device 150 in the distal portion of the delivery catheter 130 can be directed through the patient's venous or arterial system using a magnetic navigation system, in which two or more large magnets outside the patient's body are arranged to generate magnetic fields that direct the distal portion 134 of the catheter 130 I the desired direction. One example of such a magnetic navigation system supplied by Stereotaxis, Inc. of St. Louis, Mo.

Alternatively, the magnetic coupling device 150 comprises a coil of wire wound around a permeable core such as iron or ferrite, so that when current flows through said coil, device 150 is magnetically attracted to proximal surface 128, and when the coil current is switched off, device 150 releases from proximal surface 128. The current in said coil may be either direct or alternating current (DC or AC). In those embodiments in which the current for providing electromagnetic attraction to proximal surface 128 is AC, the magnetic coupling device 150 may provide a magnetic field that inductively couples with the coil in the electrode assembly 120 to provide a supplemental recharge to the electrode assembly 120 during the delivery process. Such a supplemental recharge from the magnetic coupling device 150 may ensure that there is sufficient energy stored for a test stimulation pulse (described in more detail below in connection with FIGS. 6-8) between the electrodes 124 and 126 during the implantation of the electrode assembly 120 (e.g., to verify the operation of the electrode assembly in the implantation site).

It should be understood that, in other embodiments, the electrode assembly 120 may be releasably retained in the delivery catheter 130 using a friction-fit engagement, a mechanical connection (e.g., a threaded engagement, a mating slot and groove engagement, etc.), or the like.

As shown in FIG. 2, an actuation member 160 may be adjusted within the delivery catheter 130 to release the electrode assembly 120 from the distal portion 134 of the delivery catheter 130. For example, after the delivery catheter 130 is directed to a position adjacent to a targeted heart chamber wall, the actuation member 160 may be adjusted to force the electrode assembly 120 away from the magnetic coupling device 150 and into the heart wall tissue 35 that was previously penetrated by the guide wire instrument 140. In this embodiment, the actuation member 160 serves as an adjustable push rod that can shift from a retracted configuration to an extended configuration so as to advance the electrode assembly 120 to a deployed position outside the distal opening 135 of the delivery catheter 130. The actuation member 160 may comprise a flexible main shaft 163 that can transmit a pushing force applied from the proximal end (e.g., outside the patient's body) to a distal section 162. As described in more detail below in connection with FIG. 3, a surgeon or other user can actuate a hand-operated trigger device 137 or the like disposed along the proximal portion 138 of the delivery catheter 130 to apply the pushing force to the actuation member 160 and thereby adjust the position of the distal section 162. The distal section 162 may have a reduced diameter that is advanced through a centering mechanism 154 so as to abut the proximal surface 128 of the electrode assembly 120 during advancement of the electrode assembly 120 over the guide wire instrument 140. The distal section 162 may transition to the reduced diameter at a shoulder 164, which is configured to abut the centering mechanism 154 when the actuation member 160 has been advanced to a predetermined extension distance (refer, for example, to distance L in FIG. 6). As such, the actuation member 160 may be used to advance the electrode assembly 120 to a selected depth into the hearth wall tissue 35, and such advancement may cease when the shoulder 164 of the actuation member 160 abuts with the centering mechanism 154. Accordingly, the heart wall tissue 35 can be protected from over advancement of the electrode assembly, which could result in the electrode assembly 120 being forced entirely through the heart wall.

Figure 3:
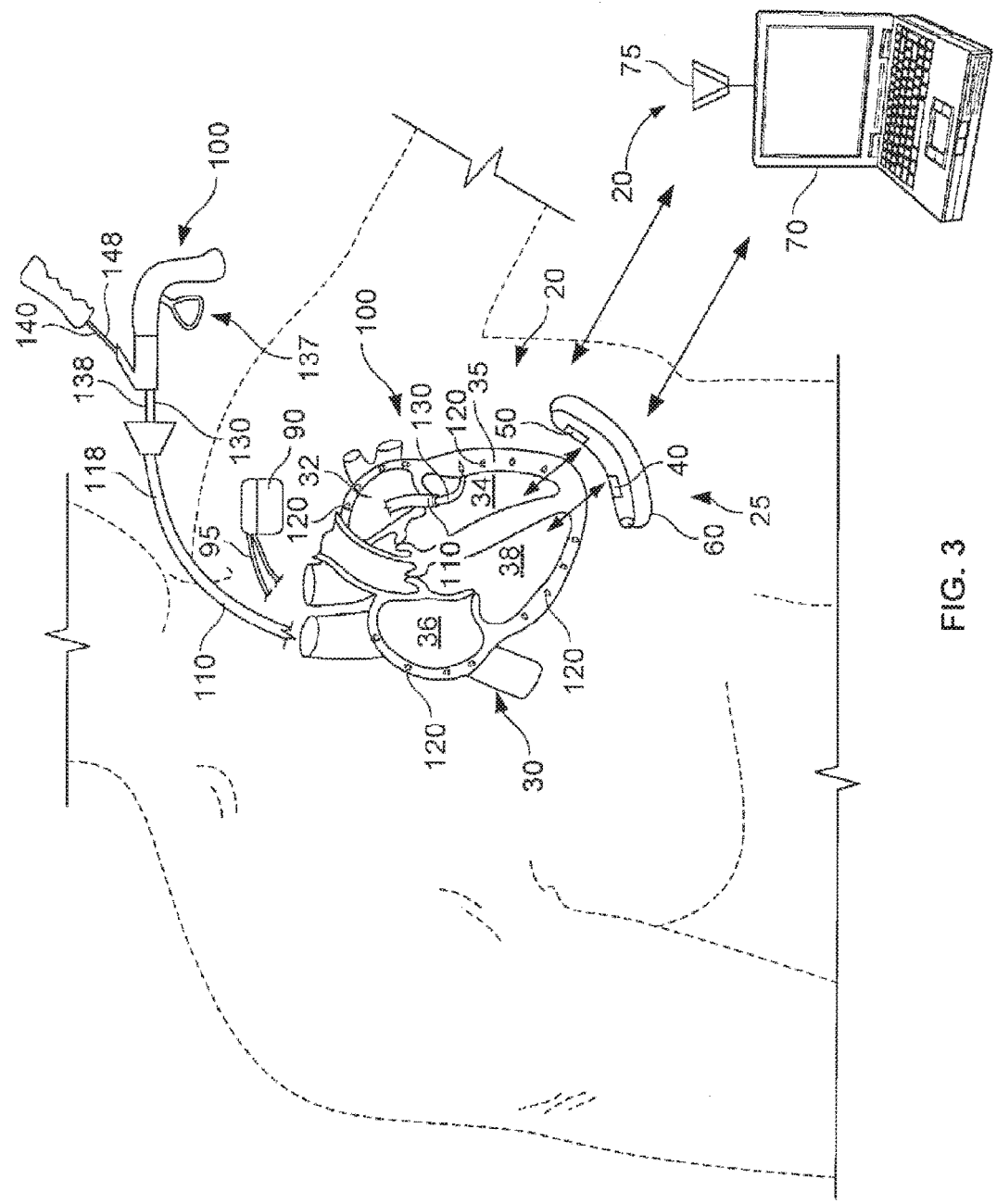
FIG. 3 is a perspective view of the electrode delivery system of FIG. 1 and an electrical stimulation system, in accordance with some embodiments.

In an alternative embodiment, the magnetic coupling device 150 and the centering mechanism 154 may be incorporated onto the main shaft 163 of the actuation member 160. In such circumstances, the distal section 162 would be an inner push rod shaft that extends fully through the main shaft of the actuation member 160. Thus, the actuation member 160, the magnetic coupling 150, and the electrode assembly 120 may be inserted into a proximal portion 138 of the delivery catheter 130 (e.g., outside the patient's body as shown in FIG. 3) and directed through the delivery catheter 130 to the targeted implantation site. In these embodiments, when the electrode assembly 120 is to be released from the magnetic coupling device 150, the distal section 162 can be moved distally relative to the main shaft 163.

Referring to FIGS. 2-3 (showing the distal portion and proximal portion of the delivery system 100, respectively), during a surgical process conducted by a surgeon or other user, the electrode assembly 120 may be disposed in the delivery catheter 130 and advanced through the guide sheath 110 toward the targeted heart chamber 32, 34, 36, or 38. As shown in FIG. 3, the guide sheath 110 may be introduced via an incision in the patient's neck and advanced through the venous system to the heart 30 (e.g., though the superior vena cava, through the right atrium 36, crossing through the atrial septum, through the left atrium 32, and into the left ventricle 34). As shown in FIG. 2, the guide sheath 110 may be configured to slidably receive the delivery catheter 130 so that the electrode assembly 120 may be loaded into the delivery catheter 130 outside the patient's body and then directed through the guide sheath 110 to the heart 30. For example, before the distal end of the delivery catheter 130 is inserted into the proximal portion 118 of the guide sheath 110 (refer to FIG. 3 for an exemplary embodiment of the proximal portion 118), the user may insert the electrode assembly 120 into the distal opening 135 of the delivery catheter 130 and force the electrode assembly 120 toward a releasably retainer device (e.g., the magnetic coupling device 150 as described in connection with FIG. 2). Then the delivery catheter 130 (with the electrode assembly 120 retained therein) can be inserted into the proximal portion 118 of the guide sheath 110 and directed therethrough to the targeted heart chamber. The user can insert the guide wire instrument 140 into the proximal portion 138 of the delivery catheter 130 (refer to FIG. 3 for an exemplary embodiment of the proximal portion 138) and advance the guide wire instrument 140 therethrough to penetrate the targeted tissue site within the targeted heart chamber. As shown in FIG. 3, the surgeon or other user may operate the trigger device 137 along the proximal portion of the delivery catheter 130 to adjust the distal section 162 of the actuation member 160 (FIG. 2). The actuation member 160 forces the electrode assembly 120 to deployed out of the distal opening 135 of the delivery catheter 130 and over the distal tip portion 142 for implantation into the heart wall tissue 35. After the electrode assembly 120 is implanted in the heart wall tissue 35, the delivery catheter 130 and the guide wire instrument 140 may be withdrawn from the proximal portion 118 of the guide sheath 110 (e.g., withdrawn fully outside of the patient's body), while the guide sheath 110 remains in the patient's body, for example, to maintain the delivery path into the targeted heart chamber. If a subsequent electrode assembly is to be delivery to the same heart chamber, a new electrode assembly 120 may be loaded into the distal opening 135 of same delivery catheter 130 (or into a new delivery catheter 130 having a similar construction) for delivery through the guide sheath 110 to a new implantation site along the targeted heart chamber wall.

In these embodiments, the guide sheath 110 can include a steering mechanism (not shown in FIGS. 2-3), such as steering wires, shape memory device, or the like, to shift the distal end during advancement into the targeted heart chamber and optionally includes at least one marker band 112 (FIG. 2) to permit viewability of the distal end of the guide sheath 110 in the patient's body using medical imaging techniques. Such a marker band 112 may aid a physician when steering the guide sheath 110 to the targeted heart chamber. Likewise, the delivery catheter 130 may also include a steering mechanism (not shown in FIGS. 2-3) so as to adjust its distal end during advance to a position adjacent the heart chamber wall and may also include at least one marker band 132 (FIG. 2) to permit viewability of the distal end of the delivery catheter 130 in the patient's body using medical imaging techniques.

Figure 4:
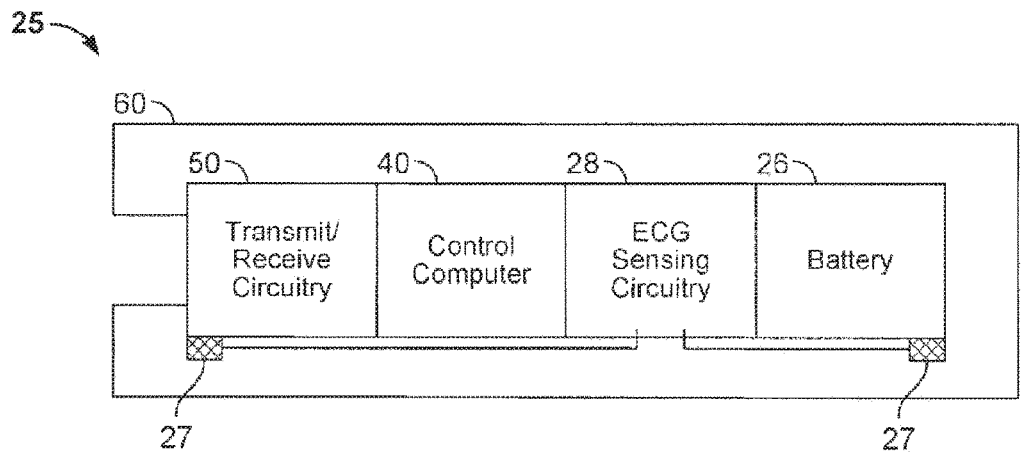
FIG. 4 is a diagram of a device of the electrical stimulation system of FIG. 3.
Figure 5:
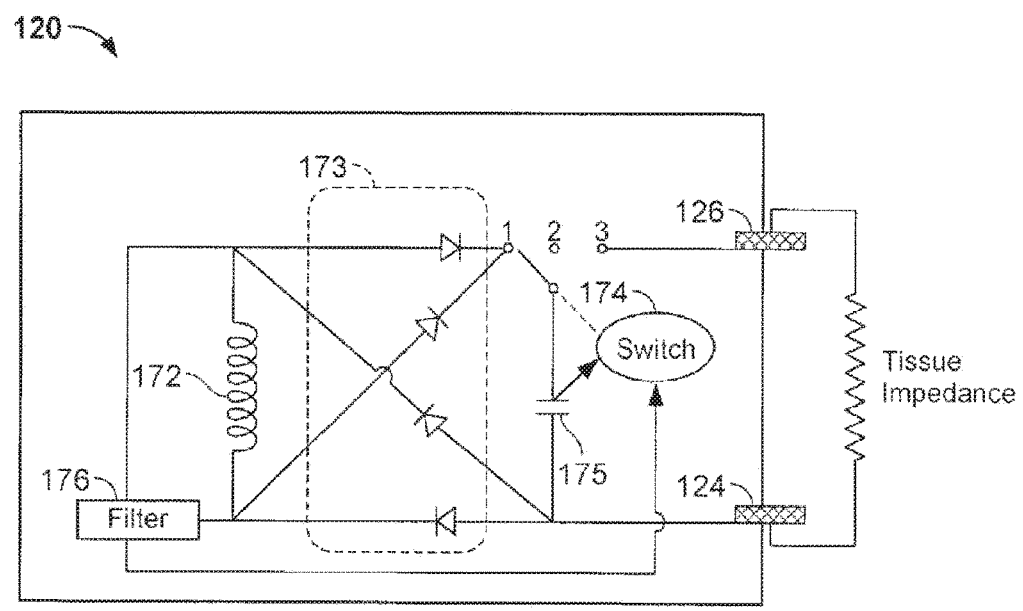
FIG. 5 is a circuit diagram of at least a portion of a wireless electrode assembly of the electrical stimulation system of FIG. 3.

Referring now to the operation of the electrical stimulation system 20 as shown, for example, in FIGS. 3-5, the wireless electrode assemblies 120 may be part of an electrical stimulation system 20 that wirelessly transmits energy to the electrode assemblies 120 for electrical stimulation of the surrounding heart wall tissue 35. As described in more detail below in connection with FIG. 5, each of the wireless electrode assemblies 120 may have an internal coil that is inductively coupled with an external power source coil to charge an electrical charge storage device (e.g., a capacitor or a battery) contained within the wireless electrode assembly 120. Also as described in more detail below, each of the wireless electrode assemblies 120 may have control circuitry or a triggering mechanism to deliver stored electrical charge to adjacent heart tissue. In alternative embodiments, one or more of the wireless electrode assemblies 120 has no energy storage device, such as a battery or capacitor. In these alternative embodiments, each wireless electrode assembly may comprise, for example, of a ferrite core and ring electrodes (e.g., bipolar electrodes) encircling the ends of the core. A number of turns of fine insulated wire may be coiled around the central portion of the core so as to receive energy from a magnetic field produced by a shaped driving signal, which causes the an stimulation pulse to pass from the coil and to the bipolar electrodes for electrical stimulation of the surrounding heart tissue.

Referring to FIG. 3, the electrical stimulation system 20 may include a stimulation controller 40 (e.g., a pacing controller) and a transmitter 50 that drives an antenna 60 for communication with the wireless electrode assemblies 120. The stimulation controller 40 can include circuitry to sense and analyze the heart's electrical activity, and to determine if and when a stimulation electrical pulse needs to be delivered and by which of the wireless electrode assemblies 120. The sensing capability may be made possible by having sensor electrodes included within the physical assembly of the stimulation controller 40. Alternatively, a single or dual lead pacemaker 90 may sense the local cardiac electrogram and transmit this information to the antenna 60 for use by the controller 40 in determining the timing of wireless electrode assembly 120 firing. In either case, the wireless electrode assembly 120 need not be provided with sensing capability, and also the wireless electrode assemblies 120 need not be equipped with the capability of communicating to the stimulation controller 40 (for example, to communicate information about sensed electrical events). In alternative embodiments, the wireless electrode assemblies 120 include local sensor circuitry to sense the local electrical activity, such as an electrogram. In these alternative embodiments, the local sensor circuitry would communicate with programmable control circuitry in the wireless electrode assembly, which would wirelessly communicate the sensed information to the controller 40 or to another implanted electrode assembly 120.

The transmitter 50—which can be in communication with, and controlled by, the stimulation controller 40—may drive an RF signal onto the antenna 60. In one embodiment, the transmitter 50 provides both (1) a charging signal to charge the electrical charge storage devices (e.g., rechargeable battery, capacitor, or the like) contained within the wireless electrode assemblies 120 via inductive coupling, and (2) an information signal, such as a pacing trigger signal, that is communicated to a selected one or more of the wireless electrode assemblies 120, commanding the selected wireless electrode assembly 120 to deliver its stored charge to the adjacent tissue. The magnetic field transmitted from the antenna 60 may be used to inductively couple with a coil in each of the electrode assemblies 120.

Still referring to FIG. 3, the stimulation controller 40 and the transmitter 50 may be housed in a single enclosure that is implantable within a patient. In such a configuration, the single enclosure device 25 may have a single energy source (e.g., battery) that may be either rechargeable or non-rechargeable. For example, as shown in FIG. 3, the stimulation controller 40 and the transmitter 50 are housed in an enclosure device 25 that is implantable along or along one or more ribs proximate to the heart 30. Such proximity between the antenna 60 and the heart 30 may facilitate efficient inductive coupling between the implanted antenna device 60 and the wireless electrode assemblies 120 embedded in the heart wall tissue 35. Accordingly, in this embodiment, the controller 40 and transmitter 50 are housed in the device 25 that is shaped generally elongate and slightly curved so that it may be anchored between two ribs of the patient, or possibly around one or more ribs. In one example, the housing for the controller 40 and transmitter 50 can be about 2 to 20 cm long and about 1 to 5 cm in diameter, or more specifically, can be about 5 to 10 cm long and about 1 to 2 cm in diameter. Also in this example, this rib-mounted housing may have a non-uniform cross-sectional shape to conform to the ribs and may be curved along its length. Such a shape of the housing for the controller 40 and transmitter 50, which allows the device to be anchored on the ribs, may provide an enclosure that is larger than conventional pacemakers, thereby providing more space for a larger battery having more stored energy. In some embodiments, the controller 40 may comprise a defibrillator circuit that discharges energy to the heart 30 through electrodes on opposing ends of the body of controller housing 25 when fibrillation is sensed. Other sizes and configurations may also be employed as is practical.

In some embodiments, the antenna 60 may be a loop antenna comprised of a long wire that is electrically connected across an electronic circuit contained within the controller/transmitter housing device 25. The electronic circuit delivers pulses of RF current to the antenna 60, generating a magnetic field in the space around the antenna 60 to charge the wireless electrode assemblies 120, as well as RF control magnetic field signals to command the wireless electrode assemblies 120 to discharge. In such embodiments, the antenna 60 may comprise a flexible conductive material so that it may be manipulated by a physician during implantation into a configuration that achieves optimum inductive coupling between the antenna 60 and the coils within the implanted wireless electrode assemblies 120. In one example, the loop antenna 60 may be about 2 to 22 cm long and about 1 to 11 cm wide, and may be about 5 to 11 cm long and about 3 to 7 cm wide. Placement of the antenna 60 over the ribs may provide a relatively large antenna to be constructed that has improved efficiency in coupling RF energy to the pacing wireless electrode assemblies 120.

In an alternative configuration, the stimulation controller 40 and the transmitter 50 may be physically separate components. As an example of such a configuration, the stimulation controller 50 may be implantable, for example in the pacemaker configuration, whereas the transmitter 50 (along with the antenna 60) may be adapted to be worn externally, such as in a harness that is worn by the patient. In the latter example, the stimulation controller 40 would have its own energy source (e.g., battery), and that energy need not be rechargeable given the relatively small energy requirements of the stimulation controller 40 as compared to the energy requirements of the transmitter 50 to be able to electrically charge the wireless electrode assemblies 120. In this case, the stimulation controller 40 would sense the local electrogram signal through a wired pacing lead, and transmit the sensed information to the external controller. Again, transmission of information, as opposed to pacing energy, has a relatively low power requirement, so a pacemaker enclosure and battery may suffice.

In some embodiments, an external programmer 70 is used to communicate with the stimulation controller 40, including after the stimulation controller 40 has been implanted. The external programmer 70 may be used to program such parameters as the timing of stimulation pulses in relation to certain sensed electrical activity of the heart, the energy level of stimulation pulses, the duration of stimulation pulse (that is, pulse width), etc. The programmer 70 includes an antenna 75 to communicate with the stimulation controller 40, using, for example, RF signals. The implantable stimulation controller 40 is accordingly equipped to communicate with the external programmer 70, using, for example, RF signals. The antenna 60 may be used to provide such communications, or alternatively, the stimulation controller 40 may have an additional antenna (not shown in FIG. 3) for external communications with the programmer 70, and in an embodiment where the transmitter 50 and antenna 60 are housed separately from the controller 40, for communications with the transmitter 50.

As shown in FIG. 3, some embodiments of the system 20 may also include a pacemaker/defibrillator device 90 and associated wired leads 95 which extend from the pacemaker/defibrillator device 90 and into one or more chambers of the heart 30. For example, the system 20 may include wired leads 95 from the pacemaker/defibrillator 90 that extend into the right atrium 36 and the right ventricle 38 while wireless electrode assemblies are disposed in the left atrium 32 and the left ventricle 34. The pacemaker/defibrillator 90 may be used to sense the internal electrogram or ECG signals, to deliver defibrillation shocks, and to communicate with the controller 40 and/or transmitter 50 as previously described.

One parameter of the wireless electrode assembly 120 that may be a factor in the design of the electrical stimulation system 20 is the stimulation energy required to pace or otherwise stimulate the ventricles 34 and 38 or other chamber of the heart 30. This energy requirement can include a typical value needed to pace ventricular myocardium, but also can include a margin to account for degradation of contact between the electrodes and tissue over time. In certain embodiments, each wireless electrode assembly 120 may require the maximum pacing threshold energy. This threshold energy is supplied to the wireless electrode assemblies between heartbeats by an external radio frequency generator (which may also be implanted), or other suitable energy source that may be implanted within the body or from a rechargeable battery contained within electrode assembly 120. In some circumstances, parameter values for some embodiments may be:

Threshold pacing voltage=2.5 Volts
Approximate tissue impedance=600 Ohms
Approximate pulse duration=0.4 mSec
Derived threshold energy=4 micro-Joules Because RF fields at frequencies higher than about 200 kHz may be attenuated by the body's electrical conductivity, and because electric fields of any frequency may be attenuated within the body, energy transmission through the body may be accomplished in some embodiments via a magnetic field at about 20-200 kHz (or by a magnetic field pulse that contains major frequency components in this range), and more particularly by transmission of magnetic fields in the range of 100-200 kHz when transmission is through relatively conductive blood and heart muscle.

In some embodiments, each of the wireless electrode assemblies 120 includes a rechargeable battery. This battery may provide power for delivering pacing energy to the tissue, and for operating communications, logic, and memory circuitry contained within the assembly. In such embodiments, the transmitter 50 and the antenna 60 (FIG. 3) may be external to the patient, and may serve to recharge the batteries within the electrode assemblies. The recharge transmitter and antenna may be incorporated into furniture, incorporated into the patient's bed, or worn by the patient (e.g., in a vest-type garment). Daily recharging for predetermined periods (e.g., about 30 minutes) may be required. In these circumstances, the wireless electrode assemblies 120 may be autonomous pacing devices, which can sense the local electrogram and only pace when the local tissue is not refractory. Such electrodes may communicate with the programming unit 70 to receive pacing instructions and transmit data stored in local memory. In these embodiments, each wireless electrode assembly 120 may also communicate with other implanted wireless electrode assemblies 120. For example, one electrode assembly 120 in the right atrium may be designated as the "master," and all other implanted electrodes are "slaves" that pace with pre-programmed delays relative to the "master." As such, a master electrode in the right atrium may only sense the heart's sinus rhythm, and may trigger pacing of the slaves with programmed delays.

Referring to FIG. 4, an embodiment of an implantable device 25 (e.g., the rib-implanted configuration shown in FIG. 3) including the controller 40, transmitter 50, and associated antenna 60 is shown in block diagram form. Included within the device 25 is: a battery 26, which may be recharged by receiving RF energy from a source outside the body via antenna 60; ECG sensing electrodes 27 and associated sensing circuitry 28; transmitter circuitry 50 for transmitting RF energy and firing commands to the implanted wireless electrode assemblies, transmitting status information to the external programmer, receiving control instructions from the external programmer, and receiving power to recharge the battery; and a stimulation controller 40 that is programmed to control the overall functioning of the implantable device 25. In alternative embodiments, antenna 60 may receive signals from the individual wireless electrode assemblies 120 containing information regarding the local electrogram at the site of each wireless electrode assembly, and/or the antenna 60 may receive signals from an implanted pacemaker device 90 regarding the electrogram signal at the sites of one or more conventional leads implanted on the right side of the heart.

Referring to FIG. 5, some embodiments of a wireless electrode assembly 120 may include a receiver coil 172 that is capable of being inductively coupled to a magnetic field source generating a time-varying magnetic field at the location of coil 172, such as would be generated by the transmitter 50 and the antenna 60 depicted in FIG. 3. The RF current in the external antenna may be a pulsed alternating current (AC) or a pulsed DC current, and thus the current induced through the receiver coil 172 may likewise be an AC or pulsed DC current. The current induced in coil 172 may be proportional to the time rate of change of the magnetic field generated at the site of coil 172 by the external RF current source. In some embodiments, a four-diode bridge rectifier 173 may connected across the receiver coil 172 to rectify the AC or pulsed DC current that is induced in the receiver coil 172. A three-position switch device 174 may be connected so that when the switch device 174 is in a first position, the rectifier 173 produces a rectified output that is imposed across a capacitor 175 or other power storage device. As such, when the switch device 174 is in the position 1 (as is the case in FIG. 5), the capacitor 175 stores the induced electrical energy.

The switch device 174, in this example, can be a voltage-controlled device that is connected to sense a voltage across the capacitor 175 to determine when the capacitor 175 has been sufficiently charged to a specified pacing threshold voltage level. When the capacitor 175 is sensed to have reached the specified pacing threshold level, the voltage-controlled switch device 174 moves to a position 2, which disconnects the capacitor 175 from the coil 172. With the switch device 174 in the position 2, the capacitor 175 is electrically isolated and remains charged, and thus is ready to be discharged. The voltage controlled switch device 174 may comprise a solid state switch, such as a field effect transistor, with its gate connected to the output of a voltage comparator that compares the voltage on capacitor 175 to a reference voltage. The reference voltage may be set at the factory, or adjusted remotely (e.g., after being implanted) via signals sent from the physician programmer unit 70 (FIG. 3), received by coil 172 and processed by circuitry not shown in FIG. 5. The electronic circuitry contained within the wireless electrode assembly 120, including the voltage controlled switch 174, can be constructed with components that consume very little power, for example CMOS. Power for such circuitry is either taken from a micro-battery contained within the wireless electrode assembly, or supplied by draining a small amount of charge from capacitor 175.

Still referring to FIG. 5, a narrow band pass filter device 176 may also be connected across the receiver coil 172, as well as being connected to the three-position switch device 174. The band pass filter device 176 passes only a single frequency of communication signal that is induced in the coil 172. The single frequency of the communication signal that is passed by the filter device 176 may be unique for the particular wireless electrode assembly 120 as compared to other implanted wireless electrode assemblies. When the receiver coil 172 receives a short magnetic field burst at this particular frequency, the filter device 176 passes the voltage to the switch device 174, which in turn moves to a position 3. With the switch device 174 in the position 3, the capacitor 175 may be connected in series through the previously described electrodes 124 and 126 (refer also to FIG. 2), to the tissue to be stimulated. As such, at least some of the charge that is stored on the capacitor 175 is discharged through the tissue (e.g., heart wall tissue 35). When this happens, the tissue becomes electrically depolarized. In one example embodiment described in more detail below, the bipolar electrodes 124 and 126 across which stimulation pulses are provided are physically located at opposite ends (e.g., a proximal end and a distal end) of the wireless electrode assembly 120. After a predetermined, or programmed, period of time, the switch returns to position 1 so the capacitor 175 may be charged back up to the selected threshold level.

It should be noted that, for sake of clarity, the schematic diagram of FIG. 5 shows only the electrical components for energy storage and for switching, in accordance with particular embodiments of the wireless electrode assembly 120. Not necessarily shown are electronics to condition the stimulation pulse delivered to the tissues, which circuitry should be understood from the description herein. Some aspects of the pulse, for example pulse width and amplitude, may be remotely programmable via encoded signals received through the filter device 176 of the wireless electrode assembly 120. In this regard, filter 176 may be a simple band pass filter with a frequency unique to a particular wireless electrode assembly, and the incoming signal may be modulated with programming information. Alternatively, filter 176 may consist of any type of demodulator or decoder that receives analog or digital information induced by the external source in coil 172. The received information may contain a code unique to each wireless electrode assembly to command discharge of capacitor 175, along with more elaborate instructions controlling discharge parameters such as threshold voltage for firing, duration and shape of the discharge pulse, etc.

Using wireless electrode assemblies 120 of the type shown in FIG. 5, all of the implanted wireless electrode assemblies 120 may be charged simultaneously by a single burst of an RF charging field from a transmitter antenna 60. Because back reaction of the wireless electrode assemblies 120 on the antenna 60 may be small, transmitter 50 (FIG. 3) losses may be primarily due to Ohmic heating of the transmit antenna 60 during the transmit burst, Ohmic heating of the receive coil 122, and Ohmic heating of conductive body tissues by eddy currents induced in these tissues by the applied RF magnetic field. By way of comparison, if eight wireless electrode assemblies 120 are implanted and each is addressed independently for charging, the transmitter 50 may be turned ON eight times as long, which may require almost eight times more energy, the additional energy being primarily lost in heating of the transmit antenna 60 and conductive body tissues. With the wireless electrode assembly 120 of FIG. 5, however, all implanted wireless electrode assemblies can be charged simultaneously with a burst of RF current in antenna 60, and antenna and body tissue heating occurs only during the time required for this single short burst. Each wireless electrode assembly 120 is addressed independently through its filter device 176 to trigger pacing. The transmitted trigger fields can be of much smaller amplitude, and therefore lose much less energy to Ohmic heating, than the transmitted charging pulse.

Figure 6:
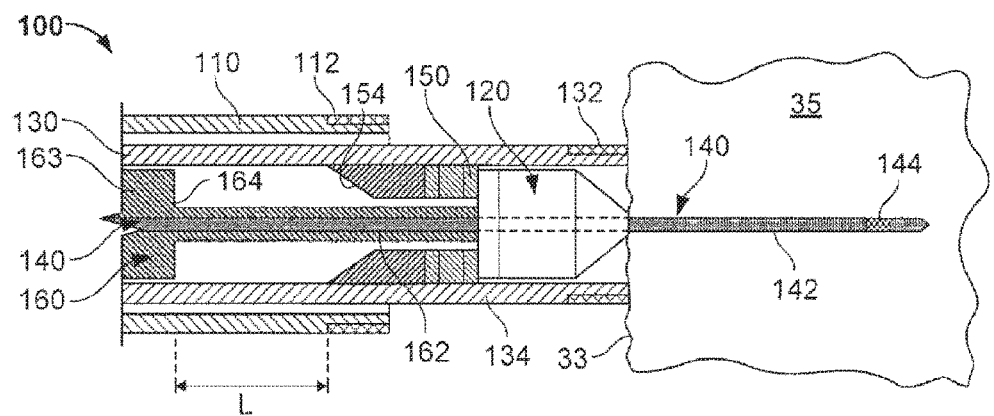
FIGS. 6-8 are partial cross-sectional views of an electrode delivery system, in accordance with some embodiments.
Figure 7:
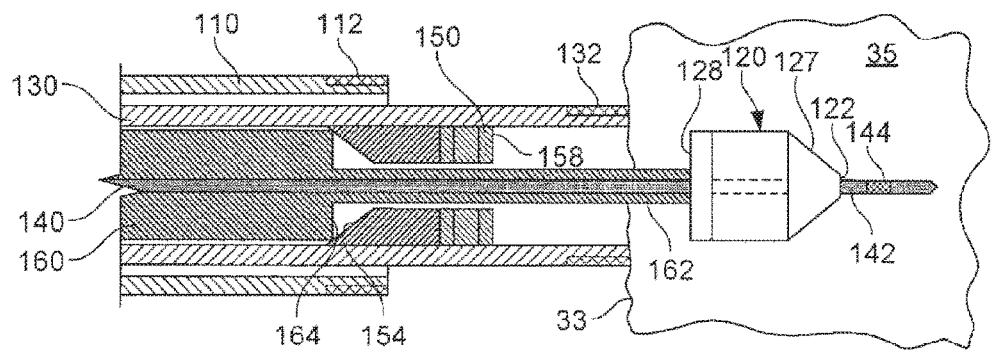
Figure 8:
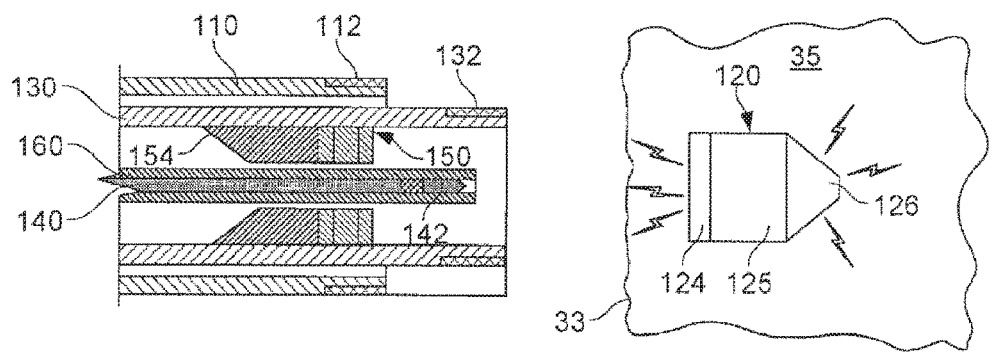

Referring now to the process of delivering the wireless electrode assemblies 120 to the heart wall tissue 35 as shown in FIGS. 6-8, the electrode delivery system 100 may be operated to initially penetrate the heart wall tissue 35 with the guide wire instrument 140 before advancing the electrode assembly 120 into the tissue 35. Such initial penetration by the guide wire instrument 140 can facilitate the subsequent penetration by the electrode assembly 120. As shown in FIG. 6, the guide sheath 110 is shown within a targeted heart chamber, and the delivery catheter 130 may be advanced to an implantation site along the endocardium 33. As previously described in connection with FIGS. 2-3, the guide sheath 110 may be introduced via an incision in the patient's neck and advanced through the venous system to the heart 30 (e.g., though the superior vena cava and into the heart 30) or via an incision in the patient's leg and advanced through one or more arteries to the heart 30 (e.g., through the femoral artery, around the aortic arch, and into the heart 30). Also as previously described, the delivery catheter 130 can be directed through the guide sheath 110 to the targeted heart chamber. The magnetic coupling device 150 may releasably retain the electrode assembly 120 in the non-deployed position inside the distal portion 134 of the delivery catheter 130. In this embodiment, the distal section 162 of the actuation member 160 is in a retracted position such that the shoulder 164 is separated from the centering mechanism 154 by at least a separation distance L.

Still referring to FIG. 6, when the delivery catheter 130 has been directed to the targeted implantation site along the endocardium 33, the distal tip portion 142 of the guide wire instrument 140 can be advanced distally to penetrate through the endocardium and into the heart wall tissue 35. As previously described, the guide wire instrument 140 may include at least one sensor electrode 144 along its distal tip portion 142 that is configured to sense local electrical activity (e.g., an electrogram or the like) and to transmit a test stimulation signal (e.g., a pacing signal) at the implantation site. In these circumstances, the guide wire instrument 140 may be used to determine if the implantation site is suitable for receipt of an electrode assembly 120 before the electrode assembly 120 is advanced into the heart wall tissue 35. The sensor electrode 144 may be in electrical communication with an electrogram or ECG monitor system (e.g., outside the patient's body) or the like so that a physician may view the local electrical activity in the heart wall tissue 35 into which the distal tip portion 142 has penetrated. Optionally, a pulse generator device or the like may be electrically connected to the proximal portion 148 (FIG. 3) of the guide wire instrument 140 so as to transmit test pacing signals to heart wall tissue 35 proximate to the sensor electrode 144.

Referring to FIG. 7, after the guide wire instrument 140 has penetrated into the heart wall tissue 35, the actuation member 160 may be adjusted so as to force the electrode assembly 120 over the guide wire instrument 140 and into the heart wall tissue 35. As previously in connection with FIGS. 2-3, a surgeon or other user may actuate a hand-operated trigger device 137 (FIG. 3) or the like disposed along the proximal portion 138 of the delivery catheter 130 to adjust the position of the distal section 162 of the actuation member 160. For example, the distal section 162 of the actuation member 162 may abut the proximal surface 128 of the electrode assembly 120 so that the actuation member 160 transmits an insertion force to the electrode assembly 120 (in response to actuation of the trigger device 137 (FIG. 3)). Such an insertion force advances the electrode assembly 120 over the guide wire instrument 140 as the guide wire channel 122 slides over the distal tip portion 142. Also, as previously described, the tissue penetration surface 127 may engage to the heart wall tissue 130 to open the tissue as the electrode assembly 120 is advanced. The actuation member 160 may be pushed forward by a distance L (FIG. 6) before the shoulder 164 abuts the centering mechanism 154. According, the depth of penetration of the electrode assembly 120 is controlled by the limited distance to which the actuation member 160 may be adjusted while advancing the electrode assembly 120. In other embodiments, the depth of penetration of the electrode assembly 120 may be controlled or monitored using stopper devices, depth markings along the trigger device 137 (FIG. 3), or the like. Advancing the electrode assembly 120 into the heart wall tissue 130 in such a controllable manner can reduce the likelihood of forcing the electrode assembly 120 fully through the heart wall.

Referring to FIG. 8, after the electrode assembly 120 is advanced over the guide wire instrument 140 to a selected depth into the heart wall tissue 35, the guide wire instrument 140 and the actuation member 160 may be withdrawn from the tissue 35. The opening in the endocardium 33 through which the actuation member 160 was passed may substantially retract after the actuation member 160 is withdrawn, thereby embedding the electrode assembly 120 in the heart wall tissue 35. In some embodiments, the embedded electrode assembly 120 may be prompted to transmit a test stimulation pulse from the electrode surfaces 124 and 126, which can verify the operability of the electrode assembly 120 in the implantation site. The actuation member 160, the guide wire instrument 140, and the delivery catheter 130 may be retracted from the guide sheath 110 while the guide sheath 110 maintains the delivery path into the targeted heart chamber. As previously described, if a subsequent electrode assembly 120 is to be delivery to the same heart chamber, a new electrode assembly 120 may be loaded into the same delivery catheter 130 (or into a new delivery catheter 130 having a similar construction) for delivery through the guide sheath 110 to a new implantation site along the targeted heart chamber wall. Thus, the subsequent electrode assembly 120 can be delivered to the targeted heart chamber without having to remove the guide sheath 110 from the heart 30, thereby reducing the likelihood of irritation or trauma to the atrial septum, the heart valves, and other heart structures caused by repeated insertions of a sheath or catheter.

Figure 9:
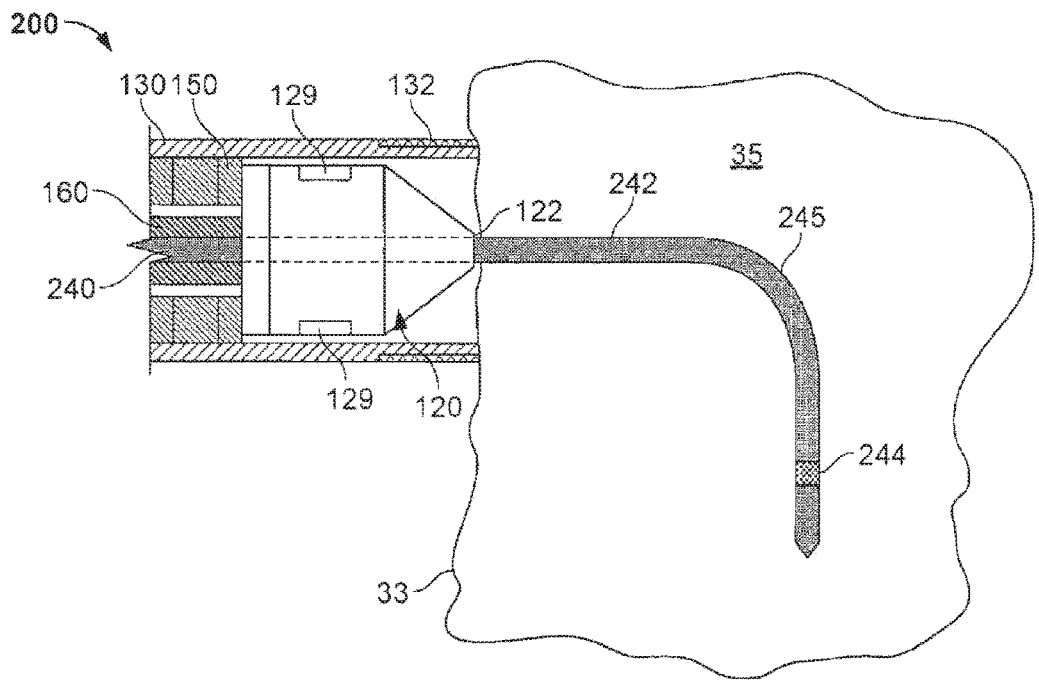
FIGS. 9-10 are partial cross-sectional views of another embodiment of an electrode delivery system.
Figure 10:
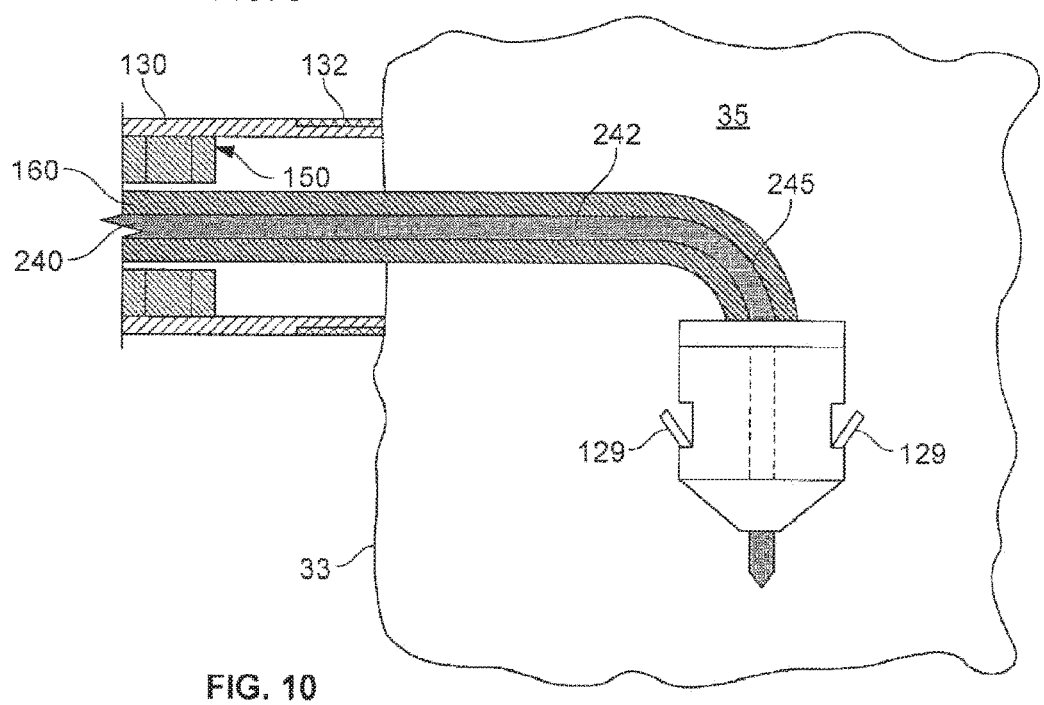

Referring now to FIGS. 9-10, in some embodiments, the electrode assembly 120 may be advanced into the heart wall tissue 35 in a direction that is non-perpendicular to the endocardial surface 33. For example, some embodiments of the guide wire instrument 240 may include a curved section 245 along the distal tip portion 242 so that the electrode assembly follows a curved path as it is advanced into the heart wall tissue 35. As shown in FIG. 9, some embodiments of an electrode delivery system 200 include a curved guide wire instrument 240 that is slidably engageable with a wireless electrode assembly 120. As described in connection with previous embodiments, the wireless electrode assembly 120 may include a guide wire channel 122 that slidably engages the guide wire instrument 240 during advancement into the heart wall tissue 35. Similar to the previously described embodiments, the electrode assembly 120 may be releasably retained in a delivery catheter 130 using a magnetic coupling device 150, and an actuation member 160 may be adjusted in a controlled manner to advance the electrode assembly 120 over the guide wire instrument 240.

Still referring to FIG. 9, when the delivery catheter 130 has been directed to the targeted implantation site along the endocardium 33, the distal tip portion 242 of the guide wire instrument 240 can penetrate through the endocardium 33 and into the heart wall tissue 35. Similar to previous embodiments, the guide wire instrument 240 may include at least one sensor electrode 244 along its distal tip portion 242 that is configured to sense local electrical activity (e.g., an electrogram or the like) and to transmit a test stimulation signal (e.g., a pacing signal) at the implantation site. The distal portion 242 of the guide wire instrument 240 may include at least one curved section 245 that permits the distal portion to penetrate a particular distance before turning and tunneling sideways into the heart wall tissue 35. The radius of curvature, the stiffness of the curved section, and the shape of the remaining portions of the distal tip portion 242 may be selected based at least in part upon the penetration resistance of the myocardium encountered by the distal tip portion 242. In some embodiments, the curved section 245 may be configured to provide the desired penetration depth and curvature into a desired tissue plane between the myocardial tissue fibers. In this embodiment, at least the curved section 245 of the distal tip portion 242 comprises an elastically deformable material such as a shape memory material (e.g., Nitinol or the like) that exhibits elasticity or super elasticity when used in the patient's body. The elastically deformable material the permits the curved section 245 to be substantially straightened while passing through the channel in the actuation member 160 (e.g., passed through the delivery catheter 130 toward the heart chamber wall). Such an elastically deformable material can return to the desired curvature after being released from the restraint in the channel of the actuation member 160.

Referring to FIG. 10, after the guide wire instrument 240 has penetrated in the heart wall tissue 35 and curved in a path non-perpendicular to the endocardial surface 33, the actuation member 160 can be adjusted to advance the electrode assembly 120 over the guide wire 240 and into the tissue 35. As the actuation member 160 applies an insertion force to the electrode assembly 120, the electrode assembly 120 may slidably engage the distal tip portion 242 and penetrate along the curved path toward the direction that is non-perpendicular to the endocardial surface. In some circumstances, the distal section 162 of the actuation member 160 may comprise a flexible material (e.g., a polymer shaft, a shaft comprising metallic coils, or the like) so that it may advance over at least a portion of the curved section 245. As previously described, the actuation member 160 may be controllably adjusted so that the electrode assembly 120 is advanced a selected distance along the guide wire instrument 240. In the embodiment shown in FIG. 10, the electrode assembly 120 includes one or more barbs 129 that extend outward from the body portion 125 when the electrode assembly 120 is deployed into the heart wall tissue 35. The barbs 129 may comprise a shape memory material (e.g., Nitinol or the like) that can flex into a non-deployed configuration (refer to FIG. 9) when the electrode assembly 120 is releasably retained in the delivery catheter 130. The barbs 129 may be deployed as fixation devices to maintain the orientation of the electrode assembly 120 while the actuation member 160 and guide wire instrument 240 are withdrawn from the tissue 35.

Figure 11:
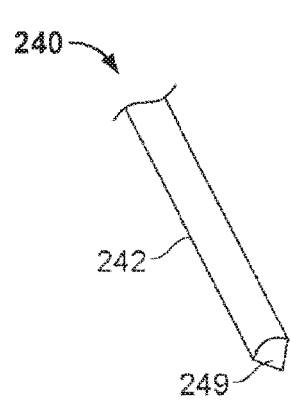
FIGS. 11-15 are perspective views of portions of guide wire instruments, in accordance with some embodiments.
Figure 12:
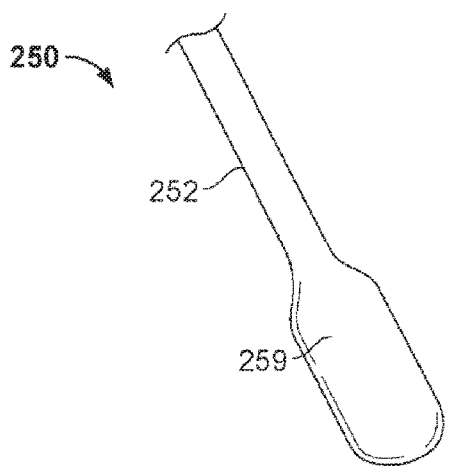
Figure 13:
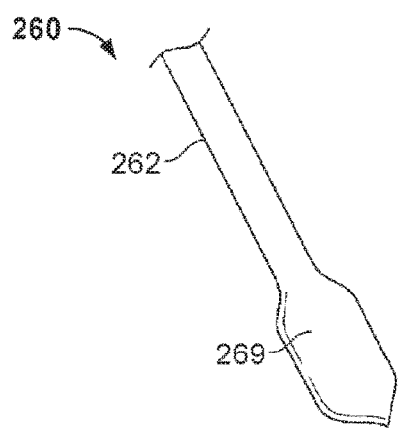

Referring to FIGS. 11-13, the distal tip portion 240 of the guide wire instrument 240 may be configured to bend during insertion into the heart wall tissue 35 so as to provide a curved insertion path. For example, as shown in FIG. 11, the distal tip portion 249 may include a pointed tip 249 that penetrates into the tissue 35 before a shape memory curved section (refer to section 245 in FIGS. 9-10) causes the distal tip portion to extend along a curved path in the heart wall tissue 35. In addition or in the alternative, a guide wire instrument 250 may be formed with a flattened tip 259 that can penetrate into the heart wall tissue 35 but subsequently bends when more rigid tissue is encountered. Thus, in some circumstances, the guide wire instrument 250 may be advanced into the heart wall tissue 35 and through the myocardium before encountering a more rigid portion of the epicardial layer. In response thereto, the flattened tip 259 of the guide wire instrument 250 may flex so that the distal portion 252 of the guide wire instrument 250 extends in a curved path through the heart wall tissue 35. In yet another embodiment, a guide wire instrument 260 may include a combination of a pointed and flattened tip 269 that can penetrate into the heart wall tissue 35 but subsequently bends when more rigid tissue is encountered. Such a guide wire instrument 250 or 260 with a bendable tip configuration may be used to form the curved path rather than the previously described shape memory curved section 245.

Figure 14:
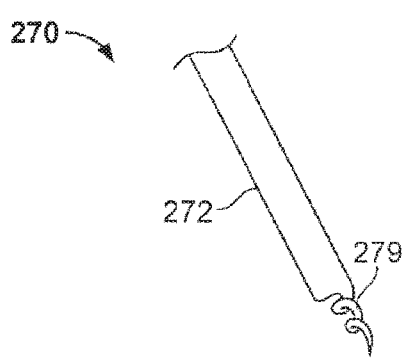
Figure 15:
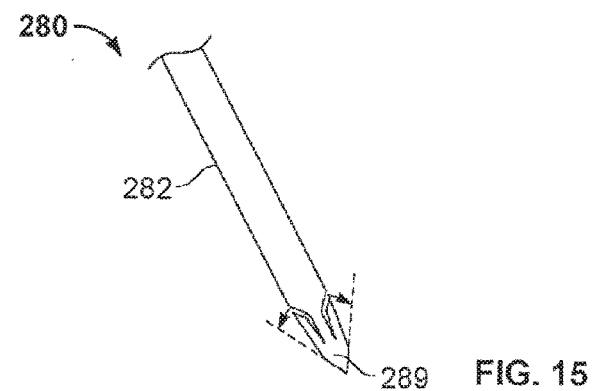

Referring now to FIGS. 14-15, some embodiments of a guide wire instrument may include a fixation device along the distal tip portion so that the guide wire instrument may be secured to the heart wall tissue 35 during the advancement of the electrode assembly 120 into the tissue 35. Such a fixation device can maintain the position of the guide wire instrument and reduce the likelihood of the distal tip portion being extended or retracted during the electrode assembly insertion process. For example, as shown in FIG. 14, some embodiments of a guide wire instrument 270 may include a fixation device in the form of a helical tine 279 extending from the distal tip portion 272. As such, the guide wire instrument 270 may be twisted as it penetrates into the heart wall tissue 35 so that the distal tip portion 272 is "screwed into" the heart wall tissue 35. After the electrode assembly 120 is advanced into the selected implantation site, the guide wire instrument 270 may be withdrawn by twisting the instrument in the opposite direction to "unscrew from" the heart wall tissue 35. In another example, as shown in FIG. 15, some embodiments of a guide wire instrument 280 may include a fixation device in the form of an adjustable barbs 289 that extend from a non-deployed configuration to a deployed configuration. In these embodiments, the adjustable barbs may be in a non-deployed configuration as the guide wire instrument 280 is passed through the delivery catheter 130 toward the heart wall tissue 35. The adjustable barbs may expand outward (e.g., away from the central guide wire axis) when no longer restrained by the surrounding instruments.

Figure 16:
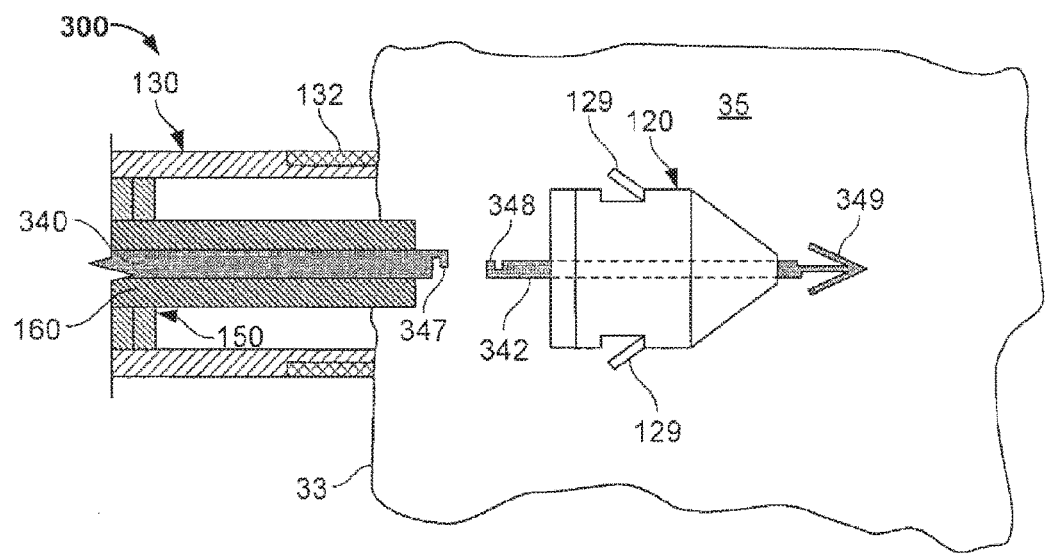
FIG. 16 is a partial cross-sectional view of an electrode delivery system having a detachable guide wire portion, in accordance with some embodiments.
Figure 17:
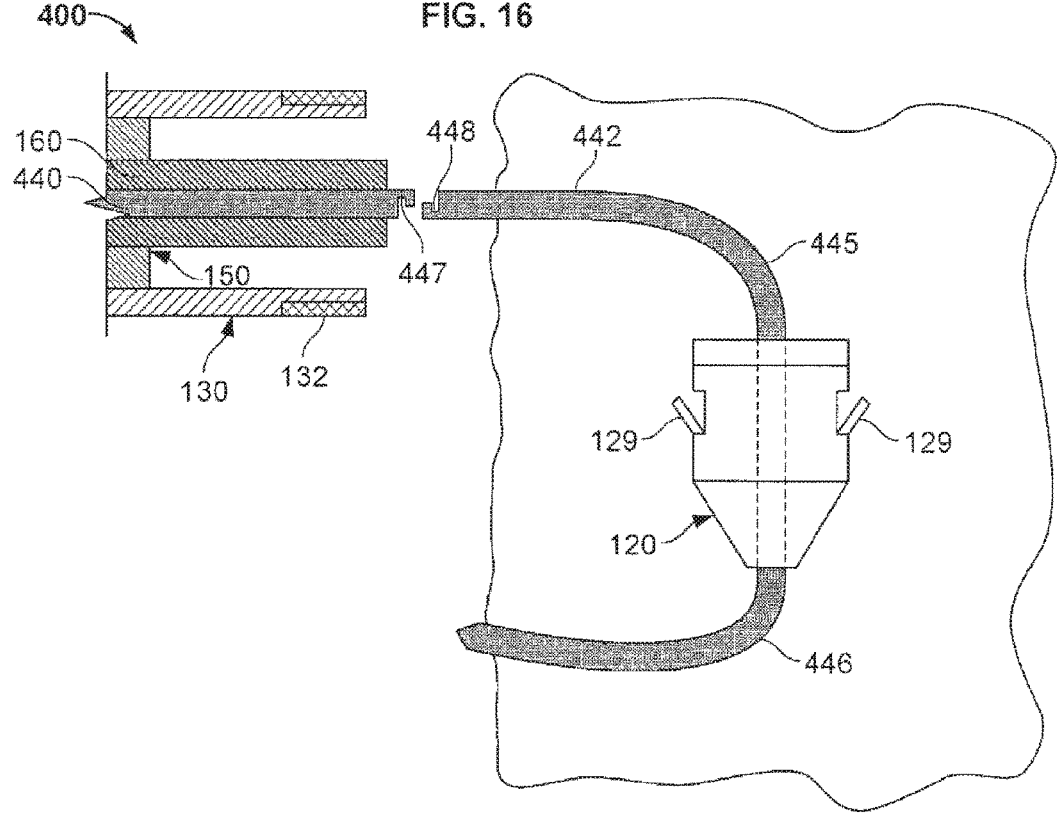
FIG. 17 is a partial cross-sectional view of another embodiment of an electrode delivery system having a detachable guide wire portion.

Referring to FIGS. 16-17, some embodiments of an electrode delivery system may include a guide wire instrument having a detachable tip portion. As such, the detachable tip portion may remain engaged with the electrode assembly 120 after it has been embedded in the heart wall tissue 35.

As shown in FIG. 16, one embodiment of an electrode delivery system 300 includes a delivery catheter 130 that can be directed through a guide sheath (not shown in FIG. 16) toward a targeted site along the endocardium 33. Similar to previously described embodiments, the electrode delivery system 300 may include a magnetic coupling device 150 to releasably retain the electrode assembly 120 in the delivery catheter 130 and may include an actuation member 160 to advance the electrode assembly 120 over the guide wire instrument 340. The guide wire instrument may be detachable along mating portions 347 and 348 so that the detachable portion 342 remains with the electrode assembly 120 in the heart wall tissue 35.

In operation of the electrode delivery system 300, the delivery catheter 130 may be directed to a targeted site on the endocardium 33, and the guide wire instrument 340 may be inserted through the endocardium 33 and into the heart wall tissue 35. The guide wire instrument 340 may include adjustable barbs 349 extending from a distal tip so as to secure the detachable portion 342 of the guide wire instrument 340 to the heart wall tissue 35. After the guide wire instrument has initiated penetration into the heart wall tissue 35, the actuation member 160 may apply an insertion force to the electrode assembly 120 so that the electrode assembly separates from the magnetic coupling device 150 and advances along the guide wire instrument 340 to a controlled depth. Similar to previously described embodiments, the electrode assembly 120 may include one or more barbs 129 that adjust to a deployed configuration so as to retain the position of the electrode assembly 120 in the heart wall tissue 35. After the electrode assembly 120 is advanced to into the heart wall tissue, the guide wire instrument 340 may be detached along the mating portions 347 and 348 so that the detachable portion 342 remains engaged with the electrode assembly 120, For example, the mating portions 347 and 348 may comprise mating tongue and groove sections that are separable when a torque is applied to the proximal end of the guide wire instrument 340 (similar to the proximal portion 148 shown in FIG. 3). Such a relative twisting action may cause the mating portions 347 and 348 to separate, thereby permitting the guide wire instrument 340 (along with the actuation member 160) to be retracted away from the heart chamber wall. The detachable tip portion 342 of the guide wire instrument 340 may serve as an anchor to the electrode assembly 120 embedded in the heart wall tissue 35. For example, the detachable tip portion 342 may reduce the likelihood of migration and changes in orientation of the electrode assembly 120 after repeated heart contractions.

Referring to FIG. 17, another embodiment of an electrode delivery system 400 includes a guide wire instrument 440 having a detachable tip portion 442 that is curved. In this embodiment, the electrode delivery system 400 includes a delivery catheter 130 that can be directed through a guide sheath (not shown in FIG. 17) toward a targeted site along the endocardium 33. Similar to previously described embodiments, the electrode delivery system 400 may include a magnetic coupling device 150 to releasably retain the electrode assembly 120 in the delivery catheter 130 and may include an actuation member 160 to advance the electrode assembly 120 over the guide wire instrument 440. The guide wire instrument 440 may be detachable along mating portions 447 and 448 so that the detachable portion 442 remains with the electrode assembly 120 in the heart wall tissue 35. Also, the guide wire instrument 440 includes two curved sections 445 and 446 so that the guide wire instrument 440 penetrates along a curved path in the heart wall tissue 35.

In operation of the electrode delivery system 400, the delivery catheter 130 may be directed to a targeted site on the endocardium 33, and the guide wire instrument 440 may be inserted through the endocardium 33 and into the heart wall tissue 35. The curved sections 445 and 446 of the guide wire instrument 440 may cause the detachable tip portion 442 to penetrate through the endocardium 33 into the heart wall tissue 35 a certain depth before curving along a path that is non-perpendicular to the endocardial surface 33 and then curve again in a path that returns toward the endocardial surface 33. After the guide wire instrument 440 has initiated penetration into the heart wall tissue 35, the actuation member 160 may apply an insertion force to the electrode assembly 120 so that the electrode assembly 120 separates from the magnetic coupling device 150 and advances along the guide wire instrument 440 for a selected advancement length. Similar to previously described embodiments, the electrode assembly 120 may include one or more barbs 129 that adjust to a deployed configuration so as to retain the position of the electrode assembly 120 in the heart wall tissue 35. After the electrode assembly 120 is advanced to into the heart wall tissue 35, the guide wire instrument 440 may be detached along the mating portions 447 and 448 so that the detachable portion 442 remains engaged with the electrode assembly 120. As such, the guide wire instrument 440 (along with the actuation member 160) can be retracted away from the heart chamber wall. The detachable tip portion 442 of the guide wire instrument 440 may serve as an anchor to the electrode assembly 120 embedded in the heart wall tissue 35. For example, the detachable tip portion 442 can maintain the orientation of the electrode assembly 120 in the heart wall tissue 35 and the second curved sections 446 may inhibit the electrode assembly 120 from forwardly migrating toward the distal tip of the detachable portion 442.

Figure 18:
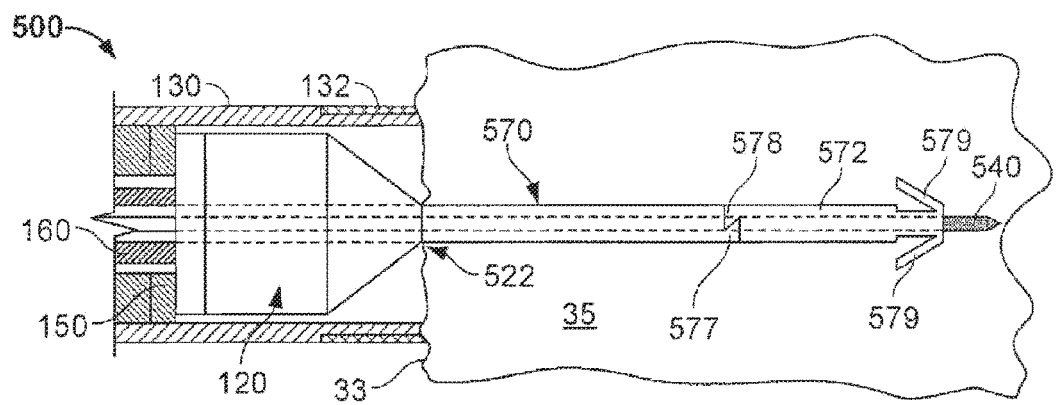
FIGS. 18-19 are partial cross-sectional views of an electrode delivery system having a detachable anchor portion, in accordance with some embodiments.
Figure 19:
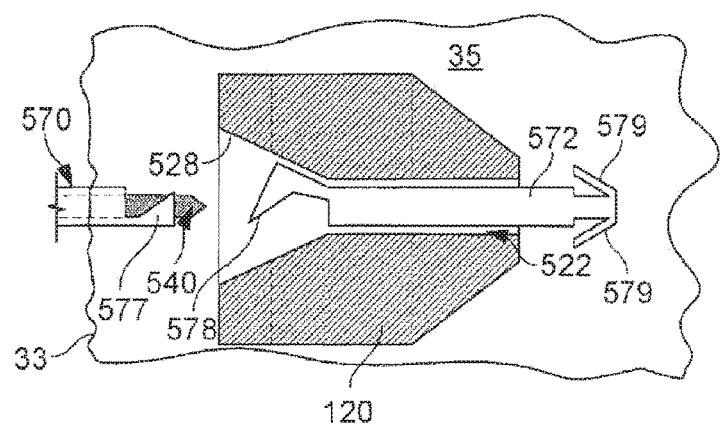

Referring to FIGS. 18-19, some embodiments of an electrode delivery system 500 may include a detachable anchor mechanism 570 that engages the electrode assembly 120 after the guide wire instrument 540 has been withdrawn from the heart wall tissue 35. In this embodiment, the electrode delivery system 500 includes a delivery catheter 130 that can be directed through a guide sheath (not shown in FIGS. 18-19) toward a targeted site along the endocardium 33. Similar to previously described embodiments, the electrode delivery system 500 may include a magnetic coupling device 150 to releasably retain the electrode assembly 120 in the delivery catheter 130 and may include an actuation member 160 to advance the electrode assembly 120 over the guide wire instrument 540 that the detachable anchor mechanism 570. The guide wire instrument 540 may be slidably engaged with the detachable anchor mechanism 570, and the wireless electrode assembly may include a guide wire channel 522 so as to slide over the guide wire instrument 540 and the detachable anchor mechanism 570. The anchor mechanism 570 can be detachable along mating portions 577 and 578 so that the detachable distal portion 572 remains with the electrode assembly 120 in the heart wall tissue 35.

In operation of the electrode delivery system 500, the delivery catheter 130 may be directed to a targeted site on the endocardium 33, and the guide wire instrument 540 may be inserted through the endocardium 33 and into the heart wall tissue 35 (refer, for example, to FIG. 18). After the guide wire instrument 540 has penetrated into the heart wall tissue 35, the anchor mechanism 570 may be advanced over the guide wire instrument 540 and into the heart wall tissue 35 to further dilate the opening formed in the endocardium 33 (refer, for example, to FIG. 18). The anchor mechanism 570 may include one or more adjustable barbs 579 extending from a distal tip portion so as to secure the anchor mechanism 570 to the heart wall tissue 35. After the guide wire instrument 540 and the anchor mechanism 570 have initiated penetration into the heart wall tissue 35, the actuation member 160 may apply an insertion force to the electrode assembly 120 so that the electrode assembly 120 separates from the magnetic coupling device 150 and advances over the anchor mechanism 570 for a selected advancement length. When the electrode assembly 120 is advanced to into the heart wall tissue 35, the anchor mechanism 570 may be detached along the mating portions 577 and 578 so that the detachable portion 572 remains engaged with the electrode assembly 120. In these circumstances, the anchor mechanism 570, the guide wire instrument 540, and the actuation member 160 can be retracted away from the heart chamber wall (refer, for example, to FIG. 19). Optionally, the guide wire instrument 540 may be withdrawn from the heart wall tissue before the electrode assembly 120 is advanced over the anchor mechanism 570.

The detachable distal portion 572 of the anchor mechanism 570 may serve as an anchor to the electrode assembly 120 embedded in the heart wall tissue 35. In this embodiment shown in FIG. 19, the mating portion 578 is bent during the detachment process (or elastically biased) so as to engage an inner conical surface 528 of the electrode assembly 120. Such an engagement reduces the likelihood of the electrode assembly 120 migrating proximally away from the adjustable barbs 579 at the distal tip of the detachable portion 572. Accordingly, the detachable distal portion 572 may serve to maintain the orientation of the electrode assembly 120 in the heart wall tissue 35.

Figure 20:
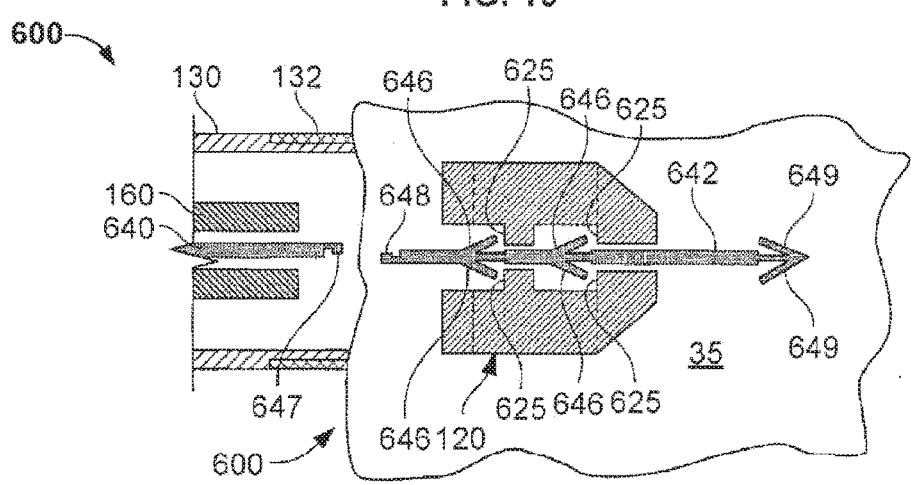
FIG. 20 is a partial cross-sectional view of an electrode delivery system having a detachable guide wire portion, in accordance with some embodiments.

Referring now to FIG. 20, some embodiments of an electrode delivery system 600 may include a guide wire instrument 640 having a detachment tip portion 642 configured to engage an inner surface of the electrode assembly 120 when implanted in the heart wall tissue 35. In this embodiment, the electrode delivery system 600 includes a delivery catheter 130 that can be directed through a guide sheath (not shown in FIG. 20) toward a targeted site along the endocardium 33. Similar to previously described embodiments, the electrode delivery system 600 may include a magnetic coupling device 150 (not shown in FIG. 20) to releasably retain the electrode assembly 120 in the delivery catheter 130 and may include an actuation member 160 to advance the electrode assembly 120 over the guide wire instrument 640. The guide wire instrument 640 may be detachable along mating portions 647 and 648 so that the detachable portion 642 remains with the electrode assembly 120 in the heart wall tissue 35. Also, the guide wire instrument 640 can include one or more adjustable stoppers 646 to engage one or more inner surfaces of the electrode assembly 120.

In operation of the electrode delivery system 600, the delivery catheter 130 may be directed to a targeted site on the endocardium 33, and the guide wire instrument 640 may be inserted through the endocardium 33 and into the heart wall tissue 35. The guide wire instrument includes one or more adjustable barbs 649 that extend from the distal tip to secure the detachable tip portion 642 to the heart tissue. The adjustable barbs 649 and the adjustable stoppers 646 may be flexed into a non-deployed configuration (e.g., pressed against the guide wire body) when the guide wire instrument is passed through a central channel of the actuation member 160. As the detachable tip portion 642 is inserted into the heart wall tissue, the adjustable barbs 649 and the adjustable stoppers may extend outwardly to a deployed configuration (as shown, for example, in FIG. 20). After the guide wire instrument 640 has initiated penetration into the heart wall tissue 35, the actuation member 160 may apply an insertion force to the electrode assembly 120 so that the electrode assembly 120 separates from the magnetic coupling device 150 and advances along the guide wire instrument 640 for a selected advancement length. The electrode assembly 120 may advance in a distal direction over the stoppers 646 during the insertion process (e.g., the stoppers 646 may partially flex inwardly to permit passage of the electrode assembly 120 in the distal direction). When the electrode assembly is advanced to the selected advancement length, the stoppers 646 may engage one or more inner surfaces 626 of the electrode assembly 120, which can reduce the likelihood of the electrode assembly 120 migrating proximally away from the adjustable barbs 649 at the distal tip of the detachable portion 642.

After the electrode assembly 120 is advanced into the heart wall tissue 35, the guide wire instrument 640 may be detached along the mating portions 647 and 648 so that the detachable portion 642 remains engaged with the electrode assembly 120. As such, the guide wire instrument 640 (along with the actuation member 160) can be retracted away from the heart chamber wall. The detachable tip portion 642 of the guide wire instrument 640 may serve as an anchor to the electrode assembly 120 embedded in the heart wall tissue 35. For instance, the detachable tip portion 642 can maintain the orientation of the electrode assembly 120 in the heart wall tissue 35.

Referring to FIGS. 21-25, some embodiments of an electrode delivery system may include a delivery catheter that is configured to releasably secure to the heart wall tissue 35 during the implantation process. Such a releasable attachment to the heart chamber wall permits the delivery catheter to maintain its position adjacent the targeted implantation site. After the electrode assembly 120 is inserted into the heart wall tissue 35, the delivery catheter may be released from the heart chamber wall and withdrawn into the guide sheath 110.

Figure 21:
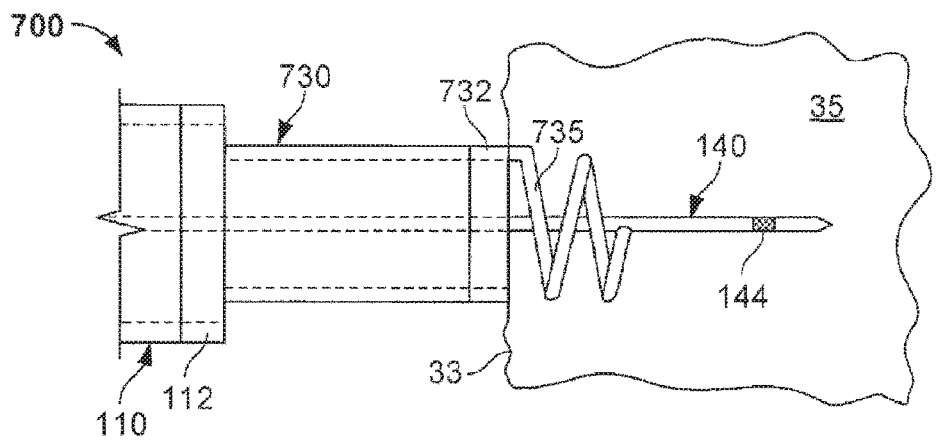
FIG. 21 is a side view of a portion of an electrode delivery system, in accordance with some embodiments.

As shown in FIG. 21, some embodiments of an electrode delivery system 700 may include a delivery catheter 730 having a fixation device to releasably engage the heart wall tissue 35. In this embodiment, the delivery catheter 730 includes a fixation device in the form of a helical tine 735 that extends distally from the tip of the delivery catheter 730. The electrode delivery system 700 includes a guide sheath 110 that slidably receives the delivery catheter 730 so that the delivery catheter can be directed toward a targeted site along the endocardium 33. Similar to previously described embodiments, the electrode delivery system 700 may include a magnetic coupling device 150 to releasably retain the electrode assembly 120 (not shown in FIG. 21) in the delivery catheter 730 and may include an actuation member 160 (not shown in FIG. 21) to advance the electrode assembly 120 over the guide wire instrument 140.

In operation, the delivery catheter 730 may be twisted as it approaches the endocardium 33 so that the helical tine 735 is "screwed into" the heart wall tissue 35. After the delivery catheter is secured to the heart wall tissue, the guide wire instrument 140 can penetrate into the heart wall tissue 35 to prepare the insertion path for the electrode assembly 120 (not shown in FIG. 21). When the guide wire instrument has penetrated into the heart wall tissue 35, the electrode assembly 120 may be advanced over the guide wire instrument 140, as described in previous embodiments, for example, in connection with FIGS. 6-8. After insertion of the electrode assembly 120, the guide wire instrument 140 and the actuation member 160 (not shown in FIG. 21) can be retracted into the delivery catheter 730, and the helical tine 735 of the delivery catheter 730 can be "unscrewed" or otherwise released from the heart wall tissue 35. It should be understood that, in some embodiments, the electrode delivery system 700 may include the delivery catheter 730 to releasably secure with the heart wall tissue 35 and may include one or more alternative guide wire instruments, such as those guide wire embodiments previously described in connection with FIGS. 9-17 and 20.

Referring to FIGS. 22-25, some embodiments of an electrode delivery system 800 may include a delivery catheter 830 having at least one adjustable fixation device to releasably engage the heart wall tissue 35. In this embodiment, the delivery catheter 830 includes adjustable fixation devices in the form of adjustable barbs 835 that can be distally extended to curl outwardly from the tip of the delivery catheter 830. The electrode delivery system 800 includes a guide sheath 110 that slidably receives the delivery catheter 830 so that the delivery catheter 830 can be directed toward a targeted site along the endocardium 33. Similar to previously described embodiments, the electrode delivery system 800 may include a magnetic coupling device 150 to releasably retain the electrode assembly 120 (not shown in FIGS. 22-25) in the delivery catheter 830 and may include an actuation member 160 (not shown in FIGS. 22-25) to advance the electrode assembly 120 over the guide wire instrument 140.

Figure 23:
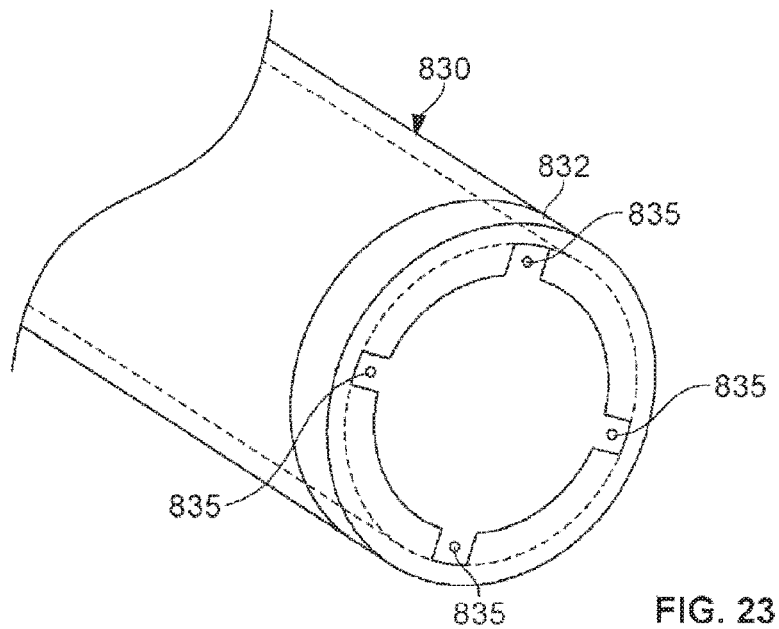
Figure 24:
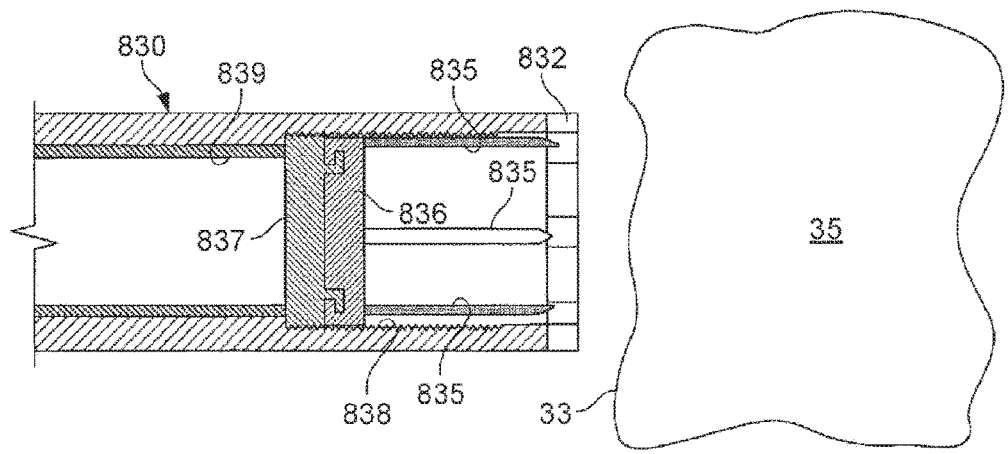
Figure 25:
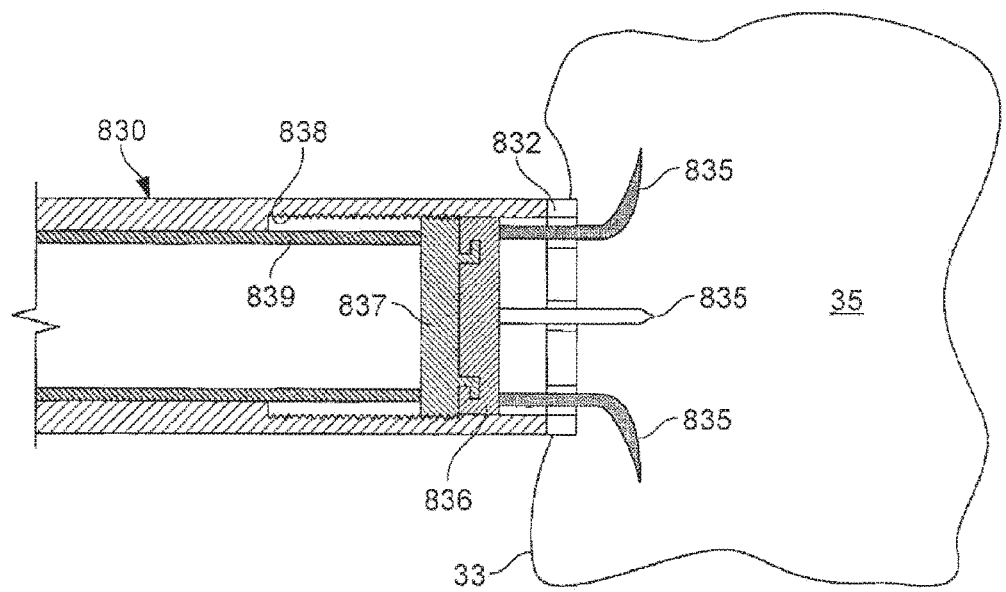

In operation, the adjustable barbs 835 may be retracted in a non-deployed configuration as the delivery catheter 830 approaches the endocardium 33 (refer, for example, to FIGS. 23-24). The adjustable barbs 835 may be coupled with a slider ring 836 that is extended and retracted by a threaded ring 837. The threaded ring 837 may be engaged by mating threads 838 along an inner distal surface of the delivery catheter 830. As such, an actuation shaft 839 that is fixedly attached to the threaded ring 837 may be twisted so as to turn the threaded ring 837 relative to the threads 838. Such a turning motion causes the threaded ring 837 to push (or pull) the slider ring 836 between the non-deployed configuration (FIG. 24) and the deployed configuration (FIG. 25). As the slider ring 836 is moved to the distal position (FIG. 25), the adjustable barbs 835 may extend distally from the delivery catheter 830 to engage the heart wall tissue 35. In this embodiment, the adjustable barbs 835 may comprise a shape memory material (e.g., Nitinol or the like) so that the barbs 835 curl outwardly away from the distal tip of the delivery catheter 830 when disposed in the deployed configuration. Such an embodiment permits the barbs to be flexed into a generally non-curved, longitudinal orientation when disposed in the non-deployed configuration (as shown, for example, in FIG. 24).

Figure 22:
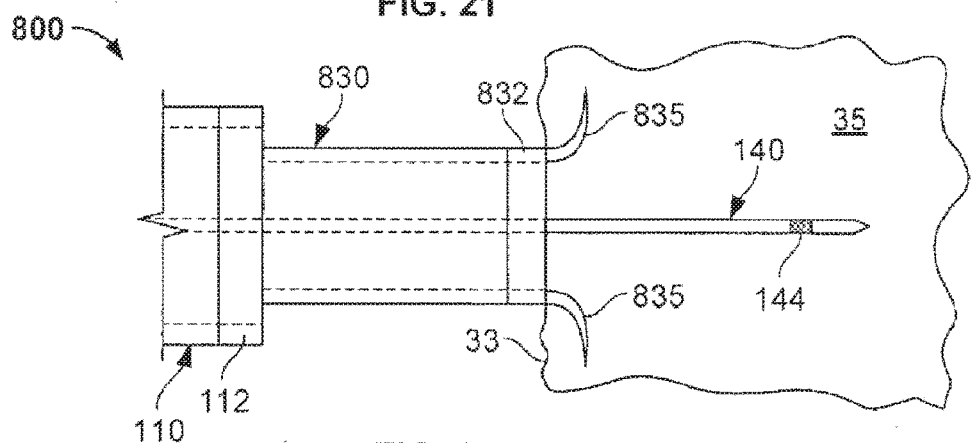
FIGS. 22-25 are views of portion of electrode delivery system, in accordance with some embodiments.

After the delivery catheter 830 is secured to the heart wall tissue 35, the guide wire instrument 140 can penetrate into the heart wall tissue 35, as shown in FIG. 22, to prepare the insertion path for the electrode assembly 120 (the electrode assembly 120 is not shown in FIG. 22). When the guide wire instrument has penetrated into the heart wall tissue 35, the electrode assembly 120 may be advanced over the guide wire instrument 140, as described in previous embodiments, for example, in connection with FIGS. 6-8. After insertion of the electrode assembly 120, the guide wire instrument 140 and the actuation member 160 (not shown in FIGS. 22-25) can be retracted into the delivery catheter 830, and the adjustable barbs 835 of the delivery catheter 830 can be released from the heart wall tissue 35. It should be understood that, in some embodiments, the electrode delivery system 800 may include the delivery catheter 830 to releasably secure with the heart wall tissue 35 and may include one or more alternative guide wire instruments, such as those guide wire embodiments previously described in connection with FIGS. 9-17 and 20.

Accordingly, in these embodiments, the delivery catheter 730 or 830 may be configured to releasably secured to the heart wall tissue 35 during the implantation process. Such a releasable attachment to the heart chamber wall permits the delivery catheter 730 or 830 to maintain its position adjacent the targeted implantation site. After the electrode assembly 120 is inserted into the heart wall tissue 35, the delivery catheter 730 or 830 may be released from the heart chamber wall and withdrawn into the guide sheath.

It should be understood from the description here that the delivery system 100 can be employed to deliver electrode assemblies 120 to locations in the body other than the human 30. For example, the guide sheath 110 and delivery catheter 130 can be used to implant one or electrode assemblies 120 to tissue in the digestive tract (e.g., stomach tissue) for electrical stimulation treatment of digestive conditions or obesity. In another example, the guide sheath 110 and delivery catheter 130 can be used to implant one or electrode assemblies 120 to tissue in the urinary tract (e.g., urinary sphincter) for electrical stimulation treatment of incontinence or other urinary conditions.

A number of embodiments of the invention have been described. Nevertheless, it will be understood that various modifications may be made without departing from the spirit and scope of the invention. Accordingly, other embodiments are within the scope of the following claims.

What is claimed is:

1. A wireless pacing electrode delivery system, comprising:
 a guide sheath including a distal end and a lumen extending to the distal end; and
 an intravascularly-deliverable medical device positionable within the lumen of the guide sheath;
 a fixation device attached to and extending away from the medical device, wherein the fixation device is configured to engage heart wall tissue, the fixation device configured to be advanced distal of the distal end of the guide sheath to engage the heart wall tissue;
 wherein the fixation device includes four tines attached to and extending distally from a ring, the four tines having a non-deployed configuration and a deployed configuration, wherein in the non-deployed configuration the four tines point distally toward the heart wall tissue to pierce into the heart wall tissue without penetrating entirely through the heart wall, and wherein the four tines are biased to curl outwardly to the deployed configuration when unconstrained to engage the heart wall tissue.

2. The system of claim 1, wherein the four tines extend in a longitudinal orientation when constrained in the non-deployed configuration.

3. The system of claim 1, wherein the four tines contact an inner wall of the delivery system when constrained in the non-deployed configuration.

4. The system of claim 1, wherein the four tines extend distal of the distal end of the guide sheath when positioned in the deployed configuration.

5. The system of claim 1, wherein the four tines are formed of a shape memory material.

6. The system of claim 5, wherein the shape memory material is nitinol.

7. The system of claim 1, wherein the four tines extend from a distal end of the intravascularly-deliverable medical device in the deployed configuration.

8. The system of claim 1, further comprising an actuator configured to deploy the four tines from the non-deployed configuration to the deployed configuration.

9. The system of claim 8, wherein the four tines are configured to moved linearly in a longitudinal direction in response to actuation of the actuator.

10. A wireless pacing electrode delivery system, comprising:
    a guide sheath including a lumen; and
    an intravascularly-deliverable medical device positionable within the lumen of the guide sheath and configured to be advanced out of a distal opening of the guide sheath to engage heart wall tissue;
    a fixation device attached to and extending away from the medical device, the fixation device including four tines attached to and extending distally from a ring;
    wherein the four tines are constrained in a non-deployed configuration when positioned within the lumen of the guide sheath and biased toward a deployed configuration when unconstrained, wherein the four tines are curled outwardly in the deployed configuration;
    wherein the four tines are configured to pierce into the heart wall tissue without penetrating entirely through the heart wall tissue to an opposite face of the heart wall tissue to engage the heart wall tissue when in the deployed configuration.

11. The system of claim 10, wherein the four tines extend in a longitudinal orientation when constrained in the non-deployed configuration.

12. The system of claim 10, wherein the four tines contact an inner wall of the delivery system when constrained in the non-deployed configuration.

13. The system of claim 10, wherein the four tines extend distal of the distal end of the guide sheath when positioned in the deployed configuration.

14. The system of claim 10, wherein the four tines are formed of a shape memory material.

15. The system of claim 14, wherein the shape memory material is nitinol.

16. The system of claim 10, wherein the four tines extend from a distal end of the intravascularly-deliverable medical device in the deployed configuration.

17. The system of claim 10, further comprising an actuator configured to deploy the four tines from the non-deployed configuration to the deployed configuration.

18. The system of claim 17, wherein the four tines are configured to moved linearly in a longitudinal direction in response to actuation of the actuator.

* * * * *